United States Patent
Piccirillo et al.

(10) Patent No.: US 10,231,824 B2
(45) Date of Patent: Mar. 19, 2019

(54) TENODESIS ANCHORING SYSTEMS AND TOOLS

(71) Applicant: DePuy Synthes Products, Inc., Raynham, MA (US)

(72) Inventors: Justin M. Piccirillo, Uxbridge, MA (US); Gerome Miller, Randolph, MA (US); Sherri Sa, New Bedford, MA (US)

(73) Assignee: MEDOS INTERNATIONAL SÁRL, Le Locle (CH)

( * ) Notice: Subject to any disclaimer, the term of this patent is extended or adjusted under 35 U.S.C. 154(b) by 107 days.

(21) Appl. No.: 15/093,948

(22) Filed: Apr. 8, 2016

(65) Prior Publication Data
US 2017/0290656 A1    Oct. 12, 2017

(51) Int. Cl.
*A61F 2/08* (2006.01)
*A61B 17/88* (2006.01)
*A61B 17/86* (2006.01)

(52) U.S. Cl.
CPC ........ *A61F 2/0811* (2013.01); *A61B 17/8872* (2013.01); *A61F 2/0805* (2013.01); *A61B 17/8645* (2013.01); *A61F 2002/0823* (2013.01); *A61F 2002/0835* (2013.01); *A61F 2002/0858* (2013.01); *A61F 2002/0864* (2013.01); *A61F 2002/0888* (2013.01)

(58) Field of Classification Search
CPC ............ A61B 17/8872; A61B 17/8894; A61B 2017/2926; A61F 2/0805
See application file for complete search history.

(56) References Cited

U.S. PATENT DOCUMENTS

| | | | |
|---|---|---|---|
| 651,949 A | 6/1900 | Lillie | |
| 775,427 A | 11/1904 | Lusted | |
| 1,426,320 A | 8/1922 | Reid | |
| 1,925,385 A | 9/1933 | Humes et al. | |
| 2,243,717 A | 5/1941 | Godoy | |

(Continued)

FOREIGN PATENT DOCUMENTS

| | | |
|---|---|---|
| AU | 2013201310 B2 | 5/2015 |
| EP | 1110510 A1 | 6/2001 |

(Continued)

OTHER PUBLICATIONS

U.S. Appl. No. 15/611,365, filed Jun. 1, 2017, Biceps Repair Device.

(Continued)

*Primary Examiner* — Suba Ganesan

(57) ABSTRACT

Systems and tools are provided for anchoring a ligament or tendon to bone. In one embodiment, a sheath is provided having a first sidewall with proximal and distal ends and a second sidewall with proximal and distal ends. The distal ends of the first and second sidewalls can be coupled to one another by a hinge pin such that the first and second sidewalls pivot relative to one another about the hinge pin. A sheath inserter tool is also provided and it can be configured to couple to the sheath and to advance the expandable sheath, with a tendon disposed therearound, into a bone hole. An expander is also provided for expanding the sheath. In this way, a tendon or ligament is delivered into the bone hole and the sheath and tendon are locked within the bone hole.

13 Claims, 17 Drawing Sheets

(56) References Cited

U.S. PATENT DOCUMENTS

| | | |
|---|---|---|
| 2,288,584 A | 6/1942 | Longfellow |
| 2,381,050 A | 8/1945 | Hardinge |
| 2,484,655 A | 10/1949 | Shreve |
| 3,073,189 A | 1/1963 | Paige |
| 3,089,359 A | 5/1963 | Poulin |
| 3,103,926 A | 9/1963 | Cochran et al. |
| 3,130,763 A | 4/1964 | Bernard et al. |
| 3,298,410 A | 1/1967 | Noboru |
| 4,503,737 A | 3/1985 | DiGiovanni |
| 4,512,344 A | 4/1985 | Barber |
| 4,592,346 A | 6/1986 | Jurgutis |
| 4,640,271 A | 2/1987 | Lower |
| 4,641,640 A | 2/1987 | Griggs |
| 4,687,392 A | 8/1987 | Bidwell |
| 4,704,055 A | 11/1987 | Guhring |
| 4,711,232 A | 12/1987 | Fischer et al. |
| 4,773,417 A | 9/1988 | Moore et al. |
| 4,851,005 A | 7/1989 | Hunt et al. |
| 4,858,810 A | 8/1989 | Intlekofer et al. |
| 4,871,289 A | 10/1989 | Choiniere |
| 4,901,717 A | 2/1990 | Moore et al. |
| 4,919,130 A | 4/1990 | Stoy et al. |
| 4,921,383 A | 5/1990 | Fischer |
| 4,960,420 A | 10/1990 | Goble et al. |
| 4,976,715 A | 12/1990 | Bays et al. |
| 4,988,351 A | 1/1991 | Paulos et al. |
| 5,026,376 A | 6/1991 | Greenberg |
| 5,029,573 A | 7/1991 | Chow |
| 5,105,690 A | 4/1992 | Lazzara et al. |
| 5,116,337 A | 5/1992 | Johnson |
| 5,129,906 A | 7/1992 | Ross et al. |
| 5,180,384 A | 1/1993 | Mikhail |
| 5,209,756 A | 5/1993 | Seedhom et al. |
| 5,211,647 A | 5/1993 | Schmieding |
| 5,226,714 A | 7/1993 | Wright |
| 5,226,890 A | 7/1993 | Ianniruberto et al. |
| 5,234,435 A | 8/1993 | Seagrave, Jr. |
| 5,242,418 A | 9/1993 | Weinstein |
| 5,258,012 A | 11/1993 | Luscombe et al. |
| 5,266,075 A | 11/1993 | Clark et al. |
| 5,273,024 A | 12/1993 | Menon et al. |
| 5,290,296 A | 3/1994 | Phillips |
| 5,290,297 A | 3/1994 | Phillips |
| 5,314,427 A | 5/1994 | Goble et al. |
| 5,320,626 A | 6/1994 | Schmieding |
| 5,325,868 A | 7/1994 | Kimmelstiel |
| 5,325,883 A | 7/1994 | Orr |
| 5,352,229 A | 10/1994 | Goble et al. |
| 5,352,231 A | 10/1994 | Brumfield et al. |
| 5,380,334 A | 1/1995 | Torrie et al. |
| 5,383,878 A | 1/1995 | Roger et al. |
| 5,385,541 A | 1/1995 | Kirsch et al. |
| 5,409,493 A | 4/1995 | Greenberg |
| 5,425,490 A | 6/1995 | Goble et al. |
| 5,445,642 A | 8/1995 | McNulty et al. |
| 5,454,811 A | 10/1995 | Huebner |
| 5,456,721 A | 10/1995 | Legrand |
| 5,478,329 A | 12/1995 | Ternamian |
| 5,505,735 A | 4/1996 | Li |
| 5,527,341 A | 6/1996 | Gogolewski et al. |
| 5,571,104 A | 11/1996 | Li |
| 5,601,558 A | 2/1997 | Torrie et al. |
| 5,601,562 A | 2/1997 | Wolf et al. |
| 5,630,805 A | 5/1997 | Ternamian |
| 5,632,748 A | 5/1997 | Beck, Jr. et al. |
| 5,651,790 A | 7/1997 | Resnick et al. |
| 5,653,763 A | 8/1997 | Errico et al. |
| 5,655,330 A | 8/1997 | Parsons, III |
| 5,658,289 A | 8/1997 | Boucher et al. |
| 5,660,186 A | 8/1997 | Bachir |
| 5,662,655 A | 9/1997 | Laboureau et al. |
| 5,662,657 A | 9/1997 | Carn |
| 5,669,925 A | 9/1997 | Saunders |
| 5,676,499 A | 10/1997 | Tukala |
| D388,171 S | 12/1997 | Fekete |
| 5,700,266 A | 12/1997 | Harryman, II |
| 5,702,398 A | 12/1997 | Tarabishy |
| 5,713,903 A | 2/1998 | Sander et al. |
| 5,720,753 A | 2/1998 | Sander et al. |
| 5,738,666 A | 4/1998 | Watson et al. |
| 5,746,743 A | 5/1998 | Greenberg |
| 5,779,707 A | 7/1998 | Bertholet et al. |
| 5,782,865 A | 7/1998 | Grotz |
| RE36,020 E | 12/1998 | Moore et al. |
| 5,895,351 A | 4/1999 | Nottage et al. |
| 5,897,565 A | 4/1999 | Foster |
| 5,899,906 A | 5/1999 | Schenk |
| 5,899,938 A | 5/1999 | Sklar et al. |
| 5,904,685 A | 5/1999 | Walawalkar |
| 5,941,882 A | 8/1999 | Jammet et al. |
| 5,948,000 A | 9/1999 | Larsen et al. |
| 5,948,001 A | 9/1999 | Larsen |
| 5,957,953 A | 9/1999 | DiPoto et al. |
| 5,961,520 A | 10/1999 | Beck, Jr. et al. |
| 5,961,521 A | 10/1999 | Roger |
| 5,968,078 A | 10/1999 | Grotz |
| 5,993,458 A | 11/1999 | Vaitekunas et al. |
| 6,027,523 A | 2/2000 | Schmieding |
| 6,117,139 A | 9/2000 | Shino |
| 6,123,711 A | 9/2000 | Winters |
| 6,143,016 A | 11/2000 | Bleam et al. |
| 6,231,606 B1 | 5/2001 | Graf et al. |
| 6,251,119 B1 | 6/2001 | Addis |
| 6,270,518 B1 | 8/2001 | Pedlick et al. |
| D448,482 S | 9/2001 | Bellofatto et al. |
| 6,283,948 B1 | 9/2001 | McKernan et al. |
| 6,306,138 B1 | 10/2001 | Clark et al. |
| 6,319,270 B1 | 11/2001 | Grafton et al. |
| 6,325,805 B1 | 12/2001 | Ogilvie et al. |
| 6,379,361 B1 | 4/2002 | Beck, Jr. et al. |
| 6,405,863 B1 | 6/2002 | Dhindsa |
| 6,443,956 B1 | 9/2002 | Ray |
| 6,464,706 B1 | 10/2002 | Winters |
| 6,517,519 B1 | 2/2003 | Rosen et al. |
| 6,517,564 B1 | 2/2003 | Grafton et al. |
| 6,533,816 B2 | 3/2003 | Sklar |
| 6,544,281 B2 | 4/2003 | ElAttrache et al. |
| 6,554,862 B2 | 4/2003 | Hays et al. |
| 6,558,389 B2 | 5/2003 | Clark et al. |
| 6,562,044 B1 | 5/2003 | Cooper |
| 6,579,295 B1 | 6/2003 | Supinski |
| 6,592,587 B1 | 7/2003 | Roger |
| 6,613,065 B2 | 9/2003 | Lajtai |
| 6,632,245 B2 | 10/2003 | Kim |
| 6,663,605 B2 | 12/2003 | Chan |
| 6,673,115 B2 | 1/2004 | Resch et al. |
| 6,712,822 B2 | 3/2004 | Re et al. |
| 6,755,815 B2 | 6/2004 | Schultz |
| 6,780,188 B2 | 8/2004 | Clark et al. |
| 6,827,722 B1 | 12/2004 | Schoenefeld |
| 6,871,740 B1 | 3/2005 | Cao |
| 6,875,214 B2 | 4/2005 | Supinski |
| 6,875,216 B2 | 4/2005 | Wolf |
| 6,887,271 B2 | 5/2005 | Justin et al. |
| 6,939,379 B2 | 9/2005 | Sklar |
| 6,942,664 B1 | 9/2005 | Voor et al. |
| 6,955,678 B2 | 10/2005 | Gabriel et al. |
| 7,074,203 B1 | 7/2006 | Johanson et al. |
| 7,083,647 B1 | 8/2006 | Sklar et al. |
| 7,104,999 B2 | 9/2006 | Overaker |
| 7,204,839 B2 | 4/2007 | Dreyfuss et al. |
| 7,235,060 B2 | 6/2007 | Kraus |
| 7,261,716 B2 | 8/2007 | Strobel et al. |
| 7,309,346 B2 | 12/2007 | Martinek |
| 7,309,355 B2 | 12/2007 | Donnelly et al. |
| 7,329,272 B2 | 2/2008 | Burkhart et al. |
| 7,341,591 B2 | 3/2008 | Grinberg |
| 7,341,592 B1 | 3/2008 | Walters et al. |
| 7,413,542 B2 | 8/2008 | Kucklick et al. |
| 7,442,202 B2 | 10/2008 | Dreyfuss |
| 7,468,074 B2 | 12/2008 | Caborn et al. |
| 7,481,830 B2 | 1/2009 | Wall et al. |
| 7,556,638 B2 | 7/2009 | Morgan et al. |
| 7,572,283 B1 | 8/2009 | Meridew |

(56) References Cited

U.S. PATENT DOCUMENTS

| | | |
|---|---|---|
| 7,611,521 B2 | 11/2009 | Lubbers et al. |
| 7,651,528 B2 | 1/2010 | Montgomery et al. |
| 7,697,861 B2 | 4/2010 | Shindo et al. |
| D615,572 S | 5/2010 | Harpaz |
| 7,713,300 B2 | 5/2010 | Meridew et al. |
| 7,736,364 B2 | 6/2010 | Stone |
| 7,766,920 B2 | 8/2010 | Ciccone et al. |
| 7,828,090 B2 | 11/2010 | Drivdahl et al. |
| 7,833,244 B2 | 11/2010 | Cerundolo |
| 7,837,731 B2 | 11/2010 | Sklar |
| 7,883,510 B2 | 2/2011 | Kim et al. |
| 7,909,826 B2 | 3/2011 | Serhan et al. |
| 7,918,288 B2 | 4/2011 | Drivdahl et al. |
| 7,959,650 B2 | 6/2011 | Kaiser et al. |
| 7,963,952 B2 | 6/2011 | Wright, Jr. et al. |
| 7,963,983 B2 | 6/2011 | Cerundolo |
| 7,967,861 B2 | 6/2011 | Montgomery et al. |
| 7,993,369 B2 | 8/2011 | Dreyfuss |
| 8,012,083 B2 | 9/2011 | Kucklick et al. |
| 8,021,403 B2 | 9/2011 | Wall et al. |
| 8,034,083 B2 | 10/2011 | Abdelgany et al. |
| 8,043,308 B2 | 10/2011 | Bittenson |
| 8,048,158 B2 | 11/2011 | Hays et al. |
| 8,051,929 B2 | 11/2011 | Drivdahl et al. |
| 8,057,524 B2 | 11/2011 | Meridew |
| 8,075,575 B2 | 12/2011 | Gonzalez-Hernandez |
| 8,123,749 B2 | 2/2012 | Serhan et al. |
| 8,128,658 B2 | 3/2012 | Kaiser et al. |
| 8,202,295 B2 | 6/2012 | Kaplan |
| 8,206,446 B1 | 6/2012 | Montgomery |
| 8,216,131 B2 | 7/2012 | Kucklick |
| 8,221,455 B2 | 7/2012 | Shurnas et al. |
| 8,221,498 B2 | 7/2012 | Boucher et al. |
| 8,226,714 B2 | 7/2012 | Beck, Jr. et al. |
| 8,231,654 B2 | 7/2012 | Kaiser et al. |
| 8,241,298 B2 | 8/2012 | Sengun et al. |
| 8,273,086 B2 | 9/2012 | Serhan et al. |
| 8,277,464 B2 | 10/2012 | Bittenson |
| 8,282,651 B2 | 10/2012 | Ciccone et al. |
| 8,292,555 B2 | 10/2012 | Shaffer |
| 8,328,716 B2 | 12/2012 | Schmieding et al. |
| 8,343,195 B2 | 1/2013 | Rathbun et al. |
| 8,348,972 B2 | 1/2013 | Soltz et al. |
| 8,361,152 B2 | 1/2013 | McCormack et al. |
| 8,377,089 B2 | 2/2013 | Lipchitz et al. |
| 8,430,909 B2 | 4/2013 | Dreyfuss |
| 8,435,293 B2 | 5/2013 | Donnelly et al. |
| 8,435,294 B2 | 5/2013 | Montgomery et al. |
| 8,465,545 B2 | 6/2013 | Montgomery et al. |
| 8,506,573 B2 | 8/2013 | Dreyfuss et al. |
| 8,512,376 B2 | 8/2013 | Thornes |
| 8,512,405 B2 | 8/2013 | Baird |
| 8,523,902 B2 | 9/2013 | Heaven et al. |
| 8,523,903 B2 | 9/2013 | Kilburn-Peterson et al. |
| 8,529,610 B2 | 9/2013 | Graf et al. |
| 8,545,535 B2 | 10/2013 | Hirotsuka et al. |
| 8,562,680 B2 | 10/2013 | Hays et al. |
| 8,608,765 B1 | 12/2013 | Jurbala |
| 8,617,197 B2 | 12/2013 | Friedman et al. |
| 8,617,219 B2 | 12/2013 | Oren et al. |
| 8,636,799 B2 | 1/2014 | Sklar et al. |
| 8,647,385 B2 | 2/2014 | Boucher et al. |
| 8,663,279 B2 | 3/2014 | Burkhart et al. |
| 8,663,325 B2 | 3/2014 | Graf et al. |
| 8,672,960 B2 | 3/2014 | Briganti et al. |
| 8,672,967 B2 | 3/2014 | DiMatteo et al. |
| 8,672,968 B2 | 3/2014 | Stone et al. |
| 8,721,650 B2 | 5/2014 | Fanton et al. |
| 8,747,470 B2 | 6/2014 | Beck, Jr. et al. |
| 8,758,227 B2 | 6/2014 | Kucklick et al. |
| 8,771,223 B2 | 7/2014 | Patton et al. |
| 8,771,303 B1 | 7/2014 | Jurbala |
| 8,778,023 B2 | 7/2014 | Sklar |
| 8,790,368 B2 | 7/2014 | Sullivan et al. |
| 8,821,383 B2 | 9/2014 | Mirza et al. |
| 8,821,527 B2 | 9/2014 | Farnan et al. |
| 8,821,557 B2 | 9/2014 | Corradi et al. |
| 8,840,665 B2 | 9/2014 | Young et al. |
| 8,845,725 B2 | 9/2014 | Barwood et al. |
| 8,870,877 B2 | 10/2014 | Koogle, Jr. |
| 8,932,354 B2 | 1/2015 | Barwood et al. |
| 8,939,983 B2 | 1/2015 | Stone et al. |
| 8,956,410 B2 | 2/2015 | Donnelly et al. |
| 9,056,010 B2 | 6/2015 | Shea et al. |
| 9,060,772 B2 | 6/2015 | Gonzalez-Hernandez |
| 9,241,783 B2 | 1/2016 | Trenhaile et al. |
| 9,289,283 B2 | 3/2016 | Baird |
| 9,301,751 B2 | 4/2016 | Sullivan et al. |
| 9,314,240 B2 | 4/2016 | Paulk et al. |
| 9,693,856 B2 | 7/2017 | Sengun et al. |
| 9,795,412 B2 | 10/2017 | Sinha |
| 2001/0021855 A1 | 9/2001 | Levinson |
| 2002/0164218 A1 | 11/2002 | Aguirre |
| 2003/0125749 A1 | 7/2003 | Yuan et al. |
| 2003/0153921 A1 | 8/2003 | Stewart et al. |
| 2003/0153926 A1 | 8/2003 | Schmieding et al. |
| 2003/0225456 A1 | 12/2003 | Ek |
| 2003/0233095 A1 | 12/2003 | Urbanski et al. |
| 2004/0068262 A1 | 4/2004 | Lemos et al. |
| 2004/0073219 A1 | 4/2004 | Skiba et al. |
| 2004/0073222 A1 | 4/2004 | Koseki |
| 2004/0193217 A1 | 9/2004 | Lubbers et al. |
| 2004/0230194 A1 | 11/2004 | Urbanski et al. |
| 2004/0267361 A1 | 12/2004 | Donnelly et al. |
| 2005/0075668 A1 | 4/2005 | Lizardi |
| 2006/0015110 A1 | 1/2006 | Pepper |
| 2006/0116685 A1 | 6/2006 | Urbanski et al. |
| 2007/0005068 A1 | 1/2007 | Sklar |
| 2007/0162124 A1 | 7/2007 | Whittaker |
| 2007/0255172 A1 | 11/2007 | Pflueger |
| 2007/0288031 A1 | 12/2007 | Dreyfuss et al. |
| 2008/0027430 A1 | 1/2008 | Montgomery et al. |
| 2008/0109038 A1 | 5/2008 | Steiner et al. |
| 2008/0161864 A1 | 7/2008 | Beck et al. |
| 2008/0215060 A1 | 9/2008 | Garcia et al. |
| 2008/0228186 A1 | 9/2008 | Gall et al. |
| 2008/0228224 A1 | 9/2008 | Sauer et al. |
| 2008/0275469 A1* | 11/2008 | Fanton ............... A61B 17/0401 606/139 |
| 2009/0138043 A1 | 5/2009 | Kohm |
| 2009/0171400 A1 | 7/2009 | van der Burg et al. |
| 2009/0192608 A1 | 7/2009 | Paulos |
| 2009/0275994 A1 | 11/2009 | Phan et al. |
| 2009/0287259 A1 | 11/2009 | Trenhaile et al. |
| 2009/0312782 A1 | 12/2009 | Park |
| 2009/0318923 A1 | 12/2009 | Burkhart et al. |
| 2010/0069958 A1 | 3/2010 | Sullivan et al. |
| 2010/0106194 A1 | 4/2010 | Bonutti et al. |
| 2010/0121348 A1* | 5/2010 | van der Burg ..... A61B 17/0401 606/139 |
| 2010/0145395 A1 | 6/2010 | Graf et al. |
| 2010/0198271 A1 | 8/2010 | Leone |
| 2010/0217393 A1 | 8/2010 | Theofilos |
| 2010/0241124 A1 | 9/2010 | Housman et al. |
| 2010/0249801 A1 | 9/2010 | Sengun et al. |
| 2011/0004247 A1 | 1/2011 | Lechmann et al. |
| 2011/0009885 A1 | 1/2011 | Graf et al. |
| 2011/0071579 A1 | 3/2011 | Reach, Jr. |
| 2011/0106013 A1 | 5/2011 | Whittaker et al. |
| 2011/0106252 A1 | 5/2011 | Barwood et al. |
| 2011/0106253 A1 | 5/2011 | Barwood et al. |
| 2011/0112550 A1 | 5/2011 | Heaven et al. |
| 2011/0112558 A1 | 5/2011 | Whayne et al. |
| 2011/0251621 A1 | 10/2011 | Sluss et al. |
| 2011/0257691 A1 | 10/2011 | Sutterlin et al. |
| 2011/0270323 A1 | 11/2011 | Olsen et al. |
| 2012/0010668 A1 | 1/2012 | Shimko |
| 2012/0057949 A1 | 3/2012 | Canizares, Jr. et al. |
| 2012/0059379 A1 | 3/2012 | Homan et al. |
| 2012/0109156 A1 | 5/2012 | Overes et al. |
| 2012/0109299 A1 | 5/2012 | Li et al. |
| 2012/0116459 A1 | 5/2012 | Nottmeier |
| 2012/0130374 A1 | 5/2012 | Bouduban et al. |
| 2012/0136357 A1 | 5/2012 | Torrie et al. |

(56) References Cited

U.S. PATENT DOCUMENTS

| | | |
|---|---|---|
| 2012/0150190 A1 | 6/2012 | Rabiner et al. |
| 2012/0211543 A1 | 8/2012 | Euteneuer |
| 2012/0215232 A1 | 8/2012 | Olsen et al. |
| 2012/0245686 A1 | 9/2012 | Park |
| 2012/0316565 A1 | 12/2012 | Stark |
| 2013/0006302 A1 | 1/2013 | Paulk et al. |
| 2013/0103054 A1 | 4/2013 | Housman |
| 2013/0125714 A1 | 5/2013 | Dahners |
| 2013/0158664 A1 | 6/2013 | Palmatier et al. |
| 2013/0190817 A1 | 7/2013 | Bouduban et al. |
| 2013/0197534 A1 | 8/2013 | Lauderbaugh et al. |
| 2013/0197591 A1 | 8/2013 | Corradi et al. |
| 2013/0238036 A1 | 9/2013 | Sinha |
| 2013/0267998 A1 | 10/2013 | Vijay et al. |
| 2013/0268010 A1 | 10/2013 | Santangelo et al. |
| 2013/0310842 A1 | 11/2013 | Winkler et al. |
| 2013/0325128 A1 | 12/2013 | Perloff et al. |
| 2013/0331942 A1 | 12/2013 | Baird |
| 2013/0338710 A1 | 12/2013 | Heaven et al. |
| 2014/0005686 A1 | 1/2014 | Patton et al. |
| 2014/0046369 A1 | 2/2014 | Heaven et al. |
| 2014/0107713 A1 | 4/2014 | Pech et al. |
| 2014/0171983 A1 | 6/2014 | Graf et al. |
| 2014/0172095 A1 | 6/2014 | Graf et al. |
| 2014/0188166 A1 | 7/2014 | Cobb et al. |
| 2014/0228898 A1 | 8/2014 | Gordon |
| 2014/0243978 A1 | 8/2014 | Beck, Jr. et al. |
| 2014/0243982 A1 | 8/2014 | Miller |
| 2014/0249579 A1 | 9/2014 | Heaven et al. |
| 2014/0257384 A1 | 9/2014 | Dreyfuss et al. |
| 2014/0277133 A1 | 9/2014 | Foerster |
| 2014/0277134 A1 | 9/2014 | ElAttrache et al. |
| 2014/0309668 A1 | 10/2014 | Sullivan et al. |
| 2014/0343604 A1 | 11/2014 | Frank |
| 2014/0364862 A1 | 12/2014 | Bennett et al. |
| 2015/0018878 A1 | 1/2015 | Rizk et al. |
| 2015/0018947 A1 | 1/2015 | Barwood |
| 2015/0173741 A1 | 6/2015 | Housman et al. |
| 2015/0190130 A1 | 7/2015 | Groh |
| 2016/0113643 A1 | 4/2016 | Diduch et al. |
| 2016/0113644 A1 | 4/2016 | Diduch et al. |
| 2016/0113756 A1 | 4/2016 | Diduch et al. |
| 2016/0113757 A1 | 4/2016 | Diduch et al. |
| 2016/0113758 A1 | 4/2016 | Diduch et al. |

FOREIGN PATENT DOCUMENTS

| | | |
|---|---|---|
| WO | 9428799 A1 | 12/1994 |
| WO | 01/30253 A1 | 5/2001 |
| WO | 2007/110863 A2 | 10/2007 |
| WO | 2012/129617 A1 | 10/2012 |
| WO | 2012138777 A1 | 10/2012 |
| WO | 2014150053 A1 | 9/2014 |

OTHER PUBLICATIONS

European Search Report for EP Application No. 17165700.0, dated Aug. 11, 2017. (12 pages).
European Search Report for EP Application No. 16166686.2, dated Sep. 20, 2016. (8 pages).
European Search Report for EP Application No. 15191002.3, dated Apr. 15, 2016. (8 pages).
European Search Report for EP Application No. 15191010.6, dated Apr. 4, 2016. (6 pages).
European Search Report for EP Application No. 15191011.4, dated Apr. 1, 2016. (6 pages).
European Search Report for EP Application No. 15191013.0, dated Apr. 14, 2016. (7 pages).
European Search Report for EP Application No. 15191001.5, dated Apr. 1, 2016. (7 pages).
U.S. Appl. No. 14/610,602, filed Jan. 30, 2015, Biceps Tenodesis Implants and Delivery Tools.
U.S. Appl. No. 14/610,609, filed Jan. 30, 2015, Biceps Tenodesis Implants and Delivery Tools.
U.S. Appl. No. 14/610,618, filed Jan. 30, 2015, Biceps Tenodesis Implants and Delivery Tools.
U.S. Appl. No. 14/610,626, filed Jan. 30, 2015, Biceps Tenodesis Anchor Implants.
U.S. Appl. No. 14/610,730, filed Jan. 30, 2015, Biceps Tenodesis Delivery Tools.
U.S. Appl. No. 14/693,276, filed Apr. 22, 2015, Biceps Repair Device.
European Search Report for EP Application No. 17165749.7, dated Aug. 21, 2017.

* cited by examiner

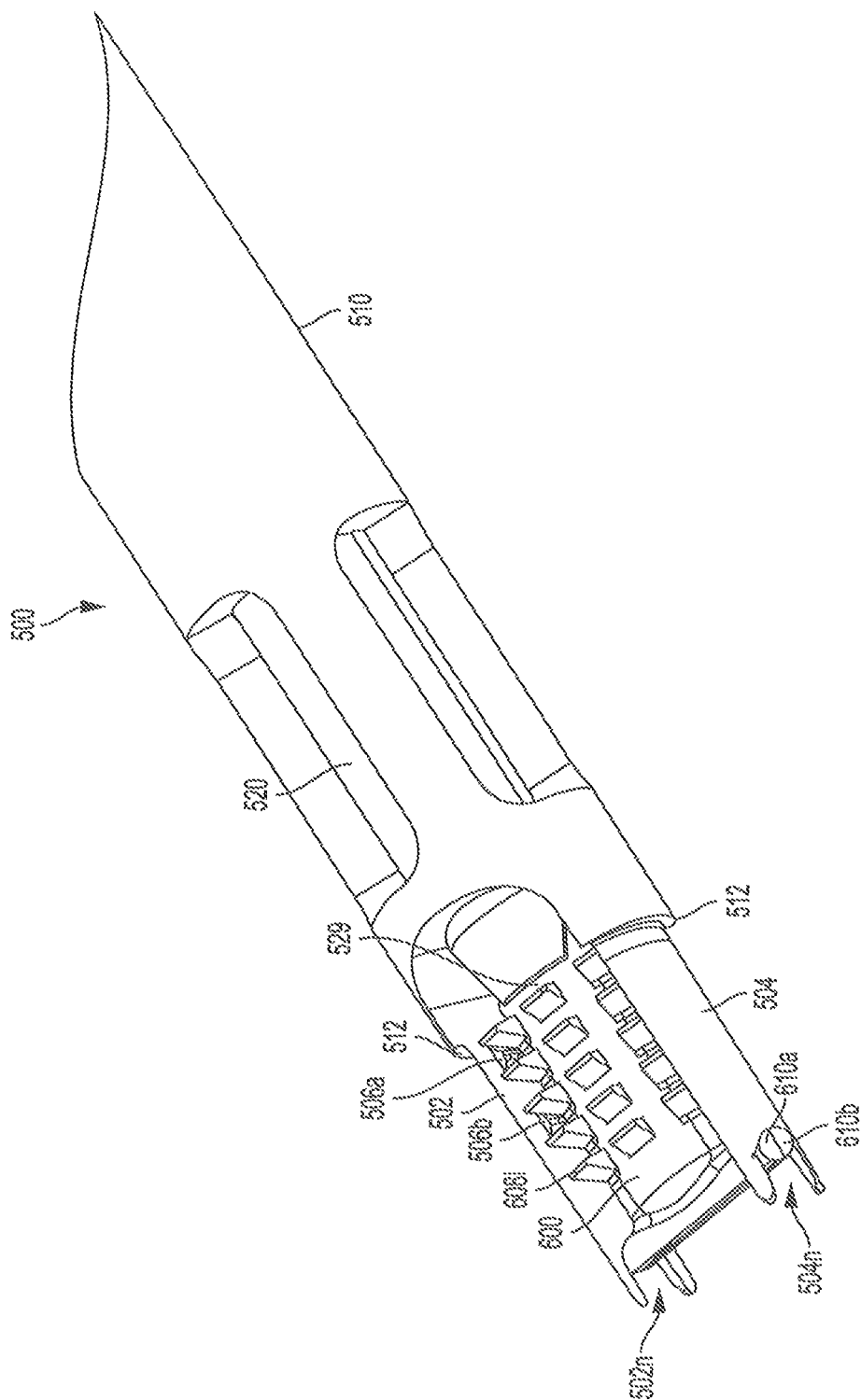

TENODESIS ANCHORING SYSTEMS AND TOOLS

FIELD

Surgical devices and methods are provided for anchoring tissue to bone, and more particularly surgical implants, delivery tools, and methods are provided for securing a biceps tendon to the humerus.

BACKGROUND

Disorders of the long head of the biceps tendon are a common source of shoulder pain and may occur in association with other diagnoses such as rotator cuff tears, superior labrum anterior posterior tears, impingement syndrome and capsular injuries, or may be present as an isolated source of shoulder pain. The treatment options for disorders of the long head of the biceps (LHB) continue to evolve and can include LHB tenodesis. In a tenodesis procedure, a suture is passed through the base of the LHB to locate the LHB in the subacromial space and to provide proximal control during the dissection. Once the suture is placed, the LHB is cut near the glenoid attachment. A sizer can be used to measure the tendon size and to thereby determine the appropriately sized bone screw. Once the screw is selected, a bone hole is drilled and a tendon fork is then used to push the tendon down into the bone hole. A bone screw is then delivered into the bone hole to anchor the tendon within the bone hole.

While current procedures can provide an effective means for anchoring a tendon to bone, they can suffer from several drawbacks. For example, current procedures require the use of numerous tools, which can lead to a prolonged procedure and increased costs. The use of a screw can also increase the risk of damage to the tendon, as rotation of the screw into the bone hole can tear or sever through the tendon. Moreover, it can be difficult to maintain the desired tension on the tendon while the screw is being implanted, as the tendon can become misaligned and or can slip during insertion of the screw. Any tension applied to the tendon during insertion of the anchor can also cause the anchor to back-out of the bone hole.

Accordingly, there remains a need for improved methods and devices for anchoring tissue to bone, and in particular for performing a biceps tenodesis.

SUMMARY

Various implants, tools and methods are provided for attaching a tendon to bone. In one embodiment, an anchor assembly is provided and includes a sheath having a first sidewall with proximal and distal ends and a second sidewall with proximal and distal ends. The distal ends of the first and second sidewalls can be coupled to one another by a hinge pin such that the first and second sidewalls pivot relative to one another about the hinge pin. The anchor assembly can also include an expander having a generally elongate cylindrical configuration. The expander can be configured to be received between the first and second sidewalls of the sheath to cause the first and second sidewalls to pivot about the hinge pin and move laterally away from one another.

While the sheath can have a variety of configurations, in one embodiment each of the first and second sidewalls can have a substantially rectangular shape with a hemi-cylindrical cavity formed on one side thereof for seating the expander. The sheath can include first and second tabs on the first and second sidewalls. The first and second tabs can be positioned at a substantial mid-portion of the first and second sidewalls between the proximal and distal ends, and the first and second tabs can be configured to receive a portion of a tool therebetween when the proximal ends of the first and second sidewalls are positioned adjacent to one another.

In other aspects, the proximal end of each of the first and second sidewalls can include a boss formed thereon and configured to engage threads on the expander to maintain alignment between the sheath and the expander. The boss on each sidewall can extend toward the other one of the first and second sidewalls such that the proximal ends of the first and second sidewalls substantially circumferentially surround the expander.

In another embodiment, the first and second sidewalls can each have an internal surface facing one another and an opposite external surface, and the external surface of each of the first and second sidewalls can have ribs formed thereon. The ribs can extend substantially perpendicular to a longitudinal axis running extending in a proximal-distal direction. In an exemplary embodiment, an external surface of each of the first and second sidewalls has a plurality of rows of ribs arranged in at least on column, each rib extending substantially perpendicular to a longitudinal axis extending in a proximal-distal direction. At least one of the ribs in a proximal-most row of ribs can have a height that is greater than a height of the ribs in the rows distal of the proximal-most row.

In other aspects, each of the first and second sidewalls can have at least one protrusion with a bore formed therein and having the hinge pin extending therethrough. For example, the distal end of the first sidewall can have a first protrusion having a bore formed therein with the hinge pin extending therethrough and a second protrusion having a bore formed therein with the hinge pin extending therethrough, and the second sidewall can have a third protrusion having a bore formed therein with the hinge pin extending therethrough and a fourth protrusion having a bore formed with the hinge pin extending therethrough. In certain aspects, the third protrusion can be positioned between the first and second protrusions, and the second protrusion can be positioned between the third and fourth protrusions.

In another embodiment, at least one of the first and second sidewalls can include a proximal tab extending radially outward from the sidewall such that the tab is effective to limit an insertion depth of the sheath into a bone hole.

At least one of the first and second sidewalls can include a suture-receiving tab formed thereon and defining a suture-receiving opening extending therethrough. In certain aspects, the suture-receiving tab can extend substantially perpendicular to a longitudinal axis of the sheath such that suture-receiving opening has a central axis that extends substantially parallel to the longitudinal axis of the sheath.

In another embodiment, a bone anchor inserter tool is provided and includes an elongate shaft having proximal and distal ends and an inner lumen extending therethrough. The distal end has first and second prongs extending distally therefrom and positioned on opposite sides of the shaft. Each prong has a first pair of bosses positioned adjacent a proximal end of each prong and a second pair of bosses positioned at adjacent a mid-portion of each prong. In one embodiment, the first pair of bosses can extend radially outward from each prong by a first distance and the second pair of bosses can extend radially outward from each prong by a second distance that is less than the first distance. Each prong can have a concave inner surface. The tool can also include other features. For example, the elongate shaft can include at least one viewing window formed in a sidewall thereof at a location proximal to the first and second prongs to allow viewing into the inner lumen of the elongate shaft.

A tendon anchoring system is also provided and in one embodiment the system includes an anchor assembly having a sheath with first and second sidewalls that are coupled at a distal end by a hinge pin such that the first and second sidewalls are configured to pivot about the hinge pin relative to one another. Each sidewall can have an anti-rotation boss formed thereon. The system can also include an inserter tool having an elongate shaft with an inner lumen extending therethrough between proximal and distal ends. The distal end can have first and second prongs extending distally therefrom from opposite sides thereof and configured to extend along opposed sides of the first and second sidewalls of the sheath such that the first and second prongs are engaged between the anti-rotation boss on each sidewall to prevent rotation of the sheath relative to the first and second prongs.

Each sidewall can include a retention boss positioned proximal of the anti-rotation boss and configured to engage an expander positioned between the first and second sidewalls of the anchor assembly. The first and second prongs can each include a proximal boss positioned proximal of the retention boss on the first and second sidewalls, and a distal boss positioned proximal of the anti-rotation boss on the first and second sidewalls and distal of the retention boss on the first and second sidewalls.

The system can also include an expander having a generally elongate cylindrical configuration and configured to be received between the first and second sidewalls of the sheath to cause the first and second sidewalls to pivot about the hinge pin and move laterally away from one another.

In other aspects, a proximal end of at least one of the first and second sidewalls has a tab extending radially outward therefrom. The tab can be received within a slot in the distal end of the elongate shaft of the inserter tool to facilitate engagement between the sheath and the inserter tool.

In another embodiment, a bone anchoring system is provided and includes a sheath having a first sidewall with proximal and distal ends and a second sidewall with proximal and distal ends. The distal ends of the first and second sidewalls are coupled to one another by a hinge pin such that the first and second sidewalls pivot relative to one another about the hinge pin. The system also includes an elongate shaft having a distal end with a distally-extending central protrusion that extends into the sheath between the first and second sidewalls. The distal end has at least first and second distally-extending side protrusions positioned on opposite sides of the central protrusion and extending along opposite outer sides of the first and second sidewalls such that the first and second distally-extending side protrusions prevent rotation of the first and second sidewalls about the hinge pin.

In one embodiment, the distally-extending central protrusion extends a distance beyond the first and second distally-extending side protrusions. In other aspects, the distally-extending central protrusion and the first and second distally-extending side protrusions define a radially extending slot therebetween that seats a proximal-most end of the first and second sidewalls. The distally-extending central protrusion can have an oblong cross-sectional shape such that the distally-extending central protrusion is prevented from rotating within the first and second sidewalls.

The elongate shaft can also include third and fourth distally-extending side protrusions positioned on opposite sides of the central protrusion and extending along opposite outer sides of the first and second sidewalls. In certain aspects, the first and second outer sidewalls each have a plurality of teeth formed thereon, and the first and third distally-extending side protrusions are positioned on opposite sides of a tooth formed on an outer surface of the first sidewall, and the second and fourth distally-extending side protrusions are positioned on opposite sides of a tooth formed on an outer surface of the second sidewall.

The elongate shaft can also include a handle slidably coupled to a proximal end of the elongate shaft. In one embodiment, the elongate shaft has proximal and distal components that are rotatably coupled to one another, and the proximal component is mated to a handle.

In yet another embodiment, a bone anchor inserter tool is provided and includes an outer shaft having proximal and distal ends and an inner lumen extending at least partially therethrough. The distal end has first and second prongs extending distally therefrom. The tool also includes an inner shaft extending through the inner lumen of the outer shaft. At least a portion of the inner shaft can be non-rotatably and freely slidably coupled to the outer shaft, and the inner shaft can have a distal end with a distally-extending central protrusion and at least first and second distally-extending side protrusions positioned on opposite sides of the central protrusion.

In one embodiment, the inner shaft can include a distal component that is non-rotatable relative to the outer shaft, and a proximal component that is rotatably coupled to the distal component. The proximal and distal components of the inner shaft can be mated by a snap-fit connection. The tool can also include a handle coupled to the proximal end of the outer shaft and coupled to the proximal component of the inner shaft. In other aspects, the inner shaft can include third and fourth distally-extending side protrusions positioned on opposite sides of the central protrusion.

A tendon anchoring system is also provided and in one embodiment the system includes an anchor assembly having a sheath with first and second sidewalls that are coupled at a distal end by a hinge pin such that the first and second sidewalls are configured to pivot about the hinge pin relative to one another. The system also includes an inserter tool having an outer shaft with an inner lumen extending therethrough between proximal and distal ends thereof. The distal end can have first and second prongs extending distally therefrom. The inserter tool also includes an inner shaft extending through the inner lumen of the outer shaft and having a distal end configured to engage the first and second sidewalls of the sheath to prevent pivotal movement of the first and second sidewalls about the hinge pin.

The anchor assembly can also include an expander configured to be received within the sheath to cause the first and second sidewalls to pivot away from one another. In one embodiment, the first and second sidewalls each have at least one retention boss formed thereon and configured to engage a proximal end of the expander when the expander is seated between the first and second sidewalls. In other aspects, the expander can have an inner lumen extending therethrough with a cross-bar extending across the inner lumen for receiving a suture therearound.

The sidewalls can have a variety of configurations. The first and second sidewalls can each include at least one anti-rotation boss formed thereon and configured to engage at least one of the first and second prongs therebetween to prevent rotation of the sheath relative to the outer shaft. In other aspects, the first and second prongs can include proximal slots formed therein that receive tabs formed on the proximal ends of the first and second sidewalls of the sheath. The tabs can be configured to slide out of the slots when the first and second sidewalls of the sheath pivotally move away from one another.

Surgical methods are also provided, and in one embodiment the method can include advancing a sheath into a bone hole, and advancing an expander into the sheath, the expander causing first and second sidewalls of the sheath to pivot relative to one another about a hinge pin coupling distal ends of the first and second sidewalls. Advancing the sheath can include, for example, manipulating an inserter tool having the sheath mounted on a distal end thereof to advance the sheath into a bone hole. In one aspect, the inserter tool can have first and second prongs that extend between the first and second sidewalls of the sheath, and the first and second prongs can include anti-rotation bosses thereon that prevent rotation of the sheath relative to the first and second prongs during advancement of the sheath into the bone hole. In another aspect, the inserter tool can include an outer shaft and an inner shaft. The inner shaft can have a distally-extending central protrusion that extends into the sheath between the first and second sidewalls, and at least first and second distally-extending side protrusions positioned on opposite sides of the central protrusion and extending along opposite outer sides of the first and second sidewalls such that the first and second distally-extending side protrusions prevent rotation of the first and second sidewalls of the sheath about the hinge pin.

BRIEF DESCRIPTION OF THE DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings:

FIG. 10 is a side perspective view of a distal end of the sheath inserter tool of FIG. 7 with the sheath of FIG. 7 coupled thereto.

DETAILED DESCRIPTION

Figure 1:
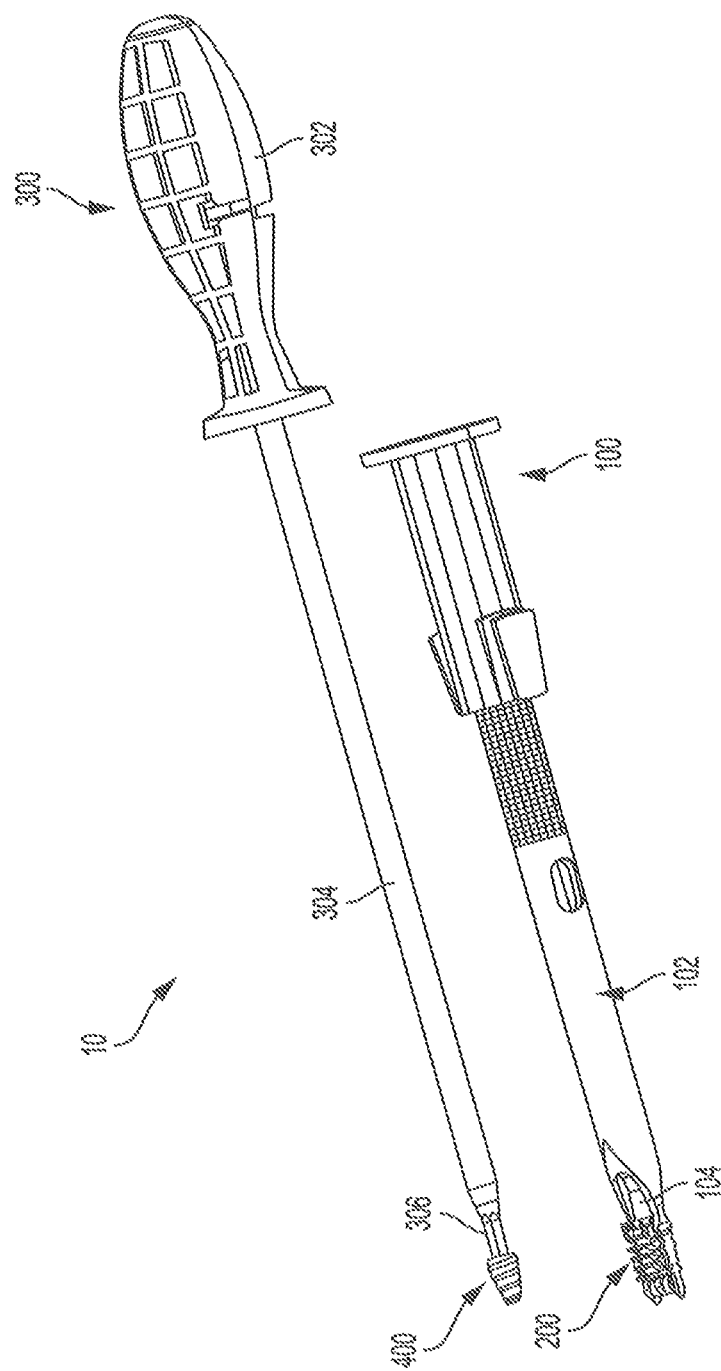
FIG. 1 side perspective view of one embodiment of a biceps tenodesis system that includes a sheath inserter tool having an expandable sheath coupled thereto, and an expander inserter tool having an expander coupled thereto.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal,"

"up," and "down" may be used herein with respect to the illustrated embodiments. However, surgical instruments may be used in many orientations and positions, and these terms are not intended to be limiting and absolute.

In general, methods and devices are provided for anchoring a ligament or tendon to bone. In an exemplary embodiment, the methods and devices are used to perform a biceps tenodesis surgery, however, a person skilled in the art will appreciate that the devices and methods can be used in various procedures and for anchoring any tissue to bone. In exemplary embodiments, various inserter tools are provided for delivering various bone anchors including an expandable sheath and an expander into a bone hole to anchor a tendon or other issue within the bone hole. The sheath can be anchored without rotating the sheath, which can eliminate or reduce a possibility of undesirable twisting of the tendon.

FIG. 1 illustrates one embodiment of a biceps tenodesis system 10 that includes a sheath inserter tool 100 having an expandable sheath 200 coupled thereto, and an expander inserter tool 300 having an expander 400 coupled thereto. The sheath inserter tool 100 has an outer shaft 102, an inner shaft 104, and a handle 106 coupled to proximal ends of the outer and inner shafts 102, 104. The sheath inserter tool 100 is configured to advance the expandable sheath 200, with a tendon disposed therearound, into a bone hole, and the expander inserter tool 300 is configured to advance the expander 400 through the outer shaft 102 of the sheath inserter tool 100 and to drive the expander 400 into the sheath 200. The expander 400 is configured to be received within a lumen extending at least partially through the expandable sheath 200 to thereby expand the sheath 200. In this way, the system 10 delivers the tendon or ligament into the bone hole and locks the sheath 200 and tendon within the bone hole. A person skilled in the art will appreciate that each of the components of the system 10 can have a variety of configurations and thus various expandable sheaths, expanders, sheath inserter tools, and expander inserter tools are disclosed herein, each of which can be used interchangeably with any of the other components disclosed herein.

FIGS. 2A-2D illustrate the sheath 200 of FIG. 1 in more detail. In general, the sheath is configured to seat a tendon therearound, and to receive the expander 400 therein, which is effective to cause the sheath to expand into bone to anchor the tendon within a bone hole. The sheath can be formed from any bio-compatible material, and, in some embodiments, it can be bio-absorbable. The shape and configuration of the sheath can vary. By way of example, the sheath 200 can be configured as described at least in U.S. patent application Ser. No. 14/610,602, entitled "Biceps Tenodesis Implants and Delivery Tools," filed Jan. 30, 2015, and in U.S. patent application Ser. No. 14/693,276, entitled "Biceps Repair Device," the contents of which are incorporated herein by reference in their entireties.

In general, the sheath 200 has an elongate substantially rectangular shape, with a length extending between a proximal end 200p and a distal end 200d that is greater than a width extending between opposing sides. The sheath 200 is configured to move from a collapsed position to an expanded position in which the sheath has more of a cylindrical configuration for conforming to the cylindrical shape of a bone hole. In this embodiment, the sheath 200 is a split sheath, with first and second separate and distinct sidewalls 202, 204 that are connected at the distal end 200d. Each sidewall 202, 204 can have a substantially rectangular shape with an outer bone engaging surface and an inner surface configured to mate with the expander 400. The sidewalls 202, 204 can define an inner lumen 206 therebetween as well as slots 200a, 200b extending along opposite sides thereof adjacent to the edges of each sidewall 202, 204.

In the illustrated embodiment, the outer surface of each sidewall 202, 204 has a substantially convex shape with a plurality of bone engaging surface features formed thereon. While the surface features can have a variety of shapes and sizes, in the illustrated embodiment the surface features are in the form of ribs or teeth 208 that are aligned in columns between the proximal and distal ends 200p, 200d as well as in rows between the opposed sides. In particular, the illustrated sidewalls 202, 204 each have three columns of teeth arranged in five rows. A person skilled in the art will appreciate that each sidewall 202, 204 can include any numbers of rows and columns of teeth, such as two or more columns and any number of rows which can vary based on the length of the sidewall. While each row can include a single elongate rib, providing multiple ribs in a single row (and thus providing multiple columns) can increase the flexibility of the sidewall 202, 204, allowing each sidewall to more readily deform against an inner surface of a bone hole. Moreover, the one or more longitudinal gaps formed between each column can help prevent damage to the tendon. The space in between the columns can provide an area for the tendon to deform into, thus preventing the tendon from being entirely pinched by the ribs.

Each tooth can have a variety of configurations. In the illustrated embodiment, each tooth is generally rectangular with four sides and a top surface that is substantially planar. The teeth 208 can all have substantially the same height such that the top surfaces all reside in the same plane. However, in one embodiment one or more of the proximal-most teeth can differ from the remainder of the teeth. For example, the proximal-most central tooth 208c can have a height that is greater than the height of the remainder of the teeth. Such a configuration can facilitate engagement with the bone hole to prevent sheath back-out. Such a configuration can also help prevent intra-operative or post-operative push-in of the implant further into the bone hole, especially where a modicum of cancellous bone exists. One or more of the teeth nearest the proximal end can also include ridges formed on the top surface thereof to further facilitate engagement with bone. For example, each tooth in the top row of teeth, including central tooth 208c, is shown having three ridges formed thereon. A person skilled in the art will appreciate that the teeth can have a variety of configurations and that in other embodiments the sidewalls 202, 204 can have threads or any other bone engaging surface features formed thereon.

The inner surface of each sidewall 202, 204 can also have a variety of configurations, but it is preferably configured to receive the expander 400 therein. In the illustrated embodiment, the inner surface of each sidewall 202, 204 has a substantially concave configuration with threads 210 formed therein for mating with corresponding threads formed on the expander 400. In this way, when the expander 400 is threaded into the sheath 200, the expander 400 will engage the threads 210 in the sheath 200 to prevent the expander 400 from backing out of the sheath 200.

Figure 2A:
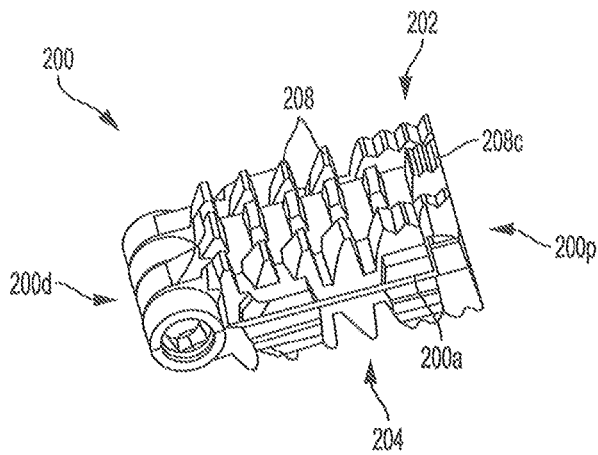
FIG. 2A is a side perspective view of the sheath of FIG. 1.
Figure 2B:
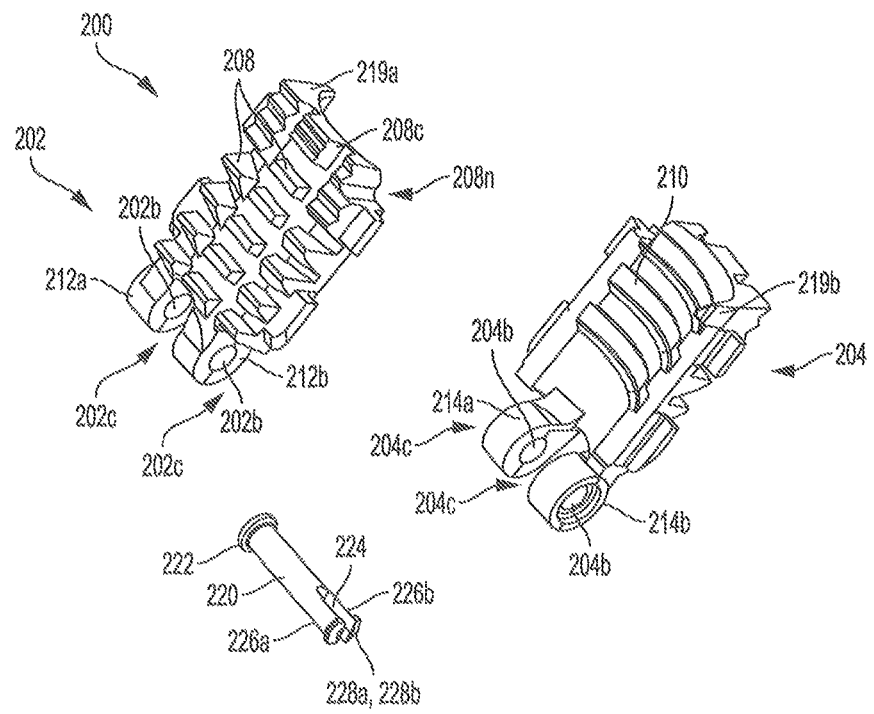
FIG. 2B is an exploded side perspective view of the sheath of FIG. 2A.
Figure 2C:
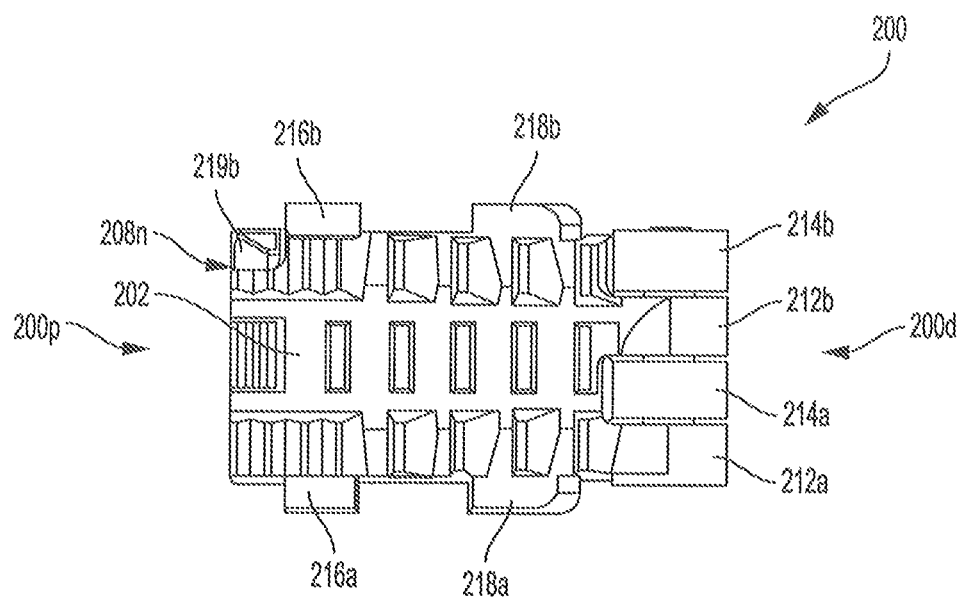
FIG. 2C is a side view of the sheath of FIG. 2A.
Figure 2D:
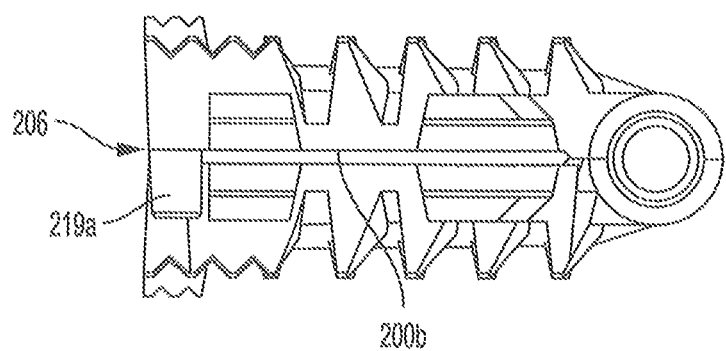
FIG. 2D is another side view of the sheath of FIG. 2A.

As indicated above, the first and second sidewalls 202, 204 are connected at their distal ends. In the illustrated embodiment, the sidewalls 202, 204 are connected by a hinge such that the sidewalls 202, 204 are pivotably movable relative to one another. As a result, the sidewalls 202, 204 can be moved away from one another at the proximal end 200p of the sheath 200 when the expander 400 is received therein. The hinged connection at the distal end 200d of the sheath 200 can be achieved using a variety of techniques. As shown in FIG. 2B, the distal end of each sidewall 202, 204 has a bore 202*bg*, 204*b* formed therein and extending across the sidewall 202, 204. The distal end of each sidewall 202, 204 also includes gaps or cutout regions 202*c*, 204*c* formed therein and offset from the other sidewall 202, 204 such that each sidewall 202, 204 has two cylindrical protrusions 212*a*, 212*b*, 214*a*, 214*b*, each having a bore formed therethrough. The two cylindrical protrusions 212*a*, 212*b* on one sidewall 202 are received between the two cylindrical protrusions 214*a*, 214*b* on the other sidewall 204 so as to align all of the bores 202*b*, 204*b* and form a single bore, as shown in FIG. 2D, for receiving a single hinge pin 220 therethrough.

The hinge pin 220, also shown in FIG. 2B, is in the form of a generally elongate cylindrical member having a head 222 at one end and opposed spring arms 226*a*, 226*b* at the opposite end. The spring arms 226*a*, 226*b* are formed by a cutout 224 extending partially into the end of the hinge pin 220. Each spring arm 226*a*, 226*b* includes a flange 228*a*, 228*b* formed around an external surface thereof. In use, the hinge pin 220 can be passed through the bore 202*b*, 204*b* formed in the protrusions at the distal end of the sidewalls 202, 204. The spring arms 226*a*, 226*b* will deflect inward while being passed through the bore, and once the flange 228*a*, 228*b* on each spring arm 226*a*, 226*b* exits the opposite side of the bore, the spring arms 226*a*, 226*b* will deflect outward returning to their resting position in which the flange 228*a*, 228*b* on each spring arm 226*a*, 226*b* will engage the end surface of protrusion 212*a* on sidewall 202 (or protrusion 214*b* on sidewall 204) so as to prevent removal of the hinge pin 220 from the sidewalls 202, 204. The hinge pin 220 is thus fixed within the bore and is not removable. The sidewalls 202, 204 are free to pivot about the hinge pin 220.

The sheath 200 can also include other features formed thereon or therein to facilitate engagement with the bone, the expander 400, or the various tools used therewith. For example, in one embodiment the sidewalls can each include one or more tabs extending outward from opposite sides thereof to engage the prongs on the inserter tool therebetween and thereby prevent rotation of the sheath relative to the tool, which will be discussed in more detail below. As shown in FIG. 2C, each sidewall 202, 204 of the sheath 200 includes left and right proximal or upper tabs 216*a*, 216*b*, 216*c*, 216*d* (only tabs 216*a*, 216*b* are shown in FIG. 2C) extending radially outward from opposite sides of a proximal end 200*p* of the sheath 200, as well as left and right distal or lower tabs 218*a*, 218*b*, 218*c*, 218*d* (only tabs 218*a*, 218*b* are shown in FIG. 2C) extending radially outward from opposite sides of a mid- or distal-portion of each sidewall 202, 204. Each of the illustrated tabs has a substantially rectangular configuration, however the tabs can have a variety of shapes and sizes.

The proximal or upper tabs 216*a*, 216*b*, 216*c*, 216*d* and the distal or lower tabs 218*a*, 218*b*, 218*c*, 218*d* can function as anti-rotation tabs. For example, the prongs of the inserter tool 100 (discussed below) can extend between the tabs on sidewall 202 and the tabs on sidewall 204 such that the tabs engage the prongs therebetween. As a result, the entire sheath 200 is prevented from rotating about an axis that extends between the sidewalls 202, 204 and perpendicular to the longitudinal axis of the sheath.

The upper tabs 216*a*, 216*b*, 216*c*, 216*d* and the lower tabs 218*a*, 218*b*, 218*c*, 218*d* can also maintain the position of the sheath 200 on the distal end of the sheath inserter tool 100. As will be discussed in more detail below, since a feature on the prongs extends between the upper and lower tabs 216*a*-*d*, 218*a*-*d* on the sheath 200, the position of the sheath 200 with respect to the prongs on the sheath inserter tool 100 is fixed.

The upper tabs 216*a*, 216*b*, 216*c*, 216*d* can also be used to advance the sheath into a bone hole, or to maintain the sheath within the bone hole during insertion of the expander into the sheath. For example, with particularly thick tendon, the tendon may apply a proximal force to the sheath. It may be desirable to apply a distal force to the tool, which in turn acts on the upper tabs, to hold the sheath in place or to advance the sheath into the bone hole.

As best shown in FIGS. 2B and 2D, each sidewall 202, 204 can also include a retention boss 219*a*, 219*b* formed on at least one side of the proximal end thereof. Each retention boss 219*a*, 219*b* can be in the form of a protrusion extending circumferentially from the terminal end of the sidewall 202, 204 such that the protrusion forms an extension of the proximal-most thread on each sidewall 202, 204. Each retention boss 219*a*, 219*b* will thus extend partially around the expander 400 to circumferentially engage the expander to maintain contact with the expander once the sheath 200 and expander 400 are implanted. Such a configuration can reduce the risk of expander dislodgment post-operatively. As shown in FIGS. 2B and 2C, in order to accommodate the retention boss (only 219*b* is shown), one of the side teeth in the proximal-most row of teeth can include a notch or cut-out 208*s* formed therein for allowing the retention boss to extend therethrough.

A person skilled in the art will appreciate that the sheath 200 can additionally or alternatively include any other suitable features. For example, the sheath 200 can include anti-collapse tabs or depth-stop tabs, discussed in more detail in U.S. patent application Ser. No. 14/610,602.

Figure 2E:
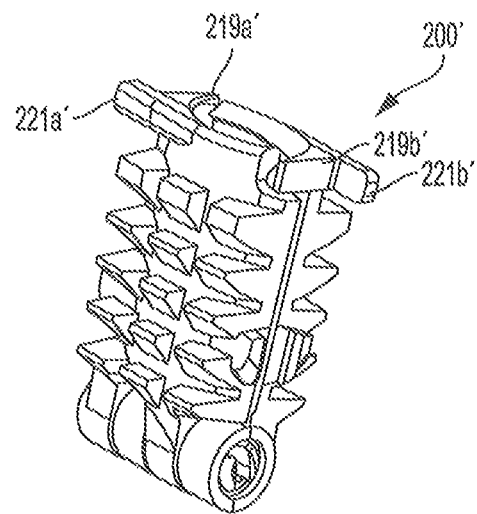
FIG. 2E is a side perspective view another embodiment of a sheath for use with a biceps tenodesis system.

By way of non-limiting example, FIG. 2E illustrates sheath 200', which is similar to sheath 200 but that includes depth-stop tabs 221*a*', 221*b*' formed thereon adjacent to the retention bosses 219*a*', 219*b*'. The depth-stop tabs 221*a*', 221*b*' extend outward from the sheath on opposed sides thereof such that they extend beyond the largest width of each sidewall of the sheath. As a result, when the sheath is inserted into a bone hole having substantially the same diameter as the sheath, the depth-stop tabs 221*a*', 221*b*' will abut against a proximal surface of the bone to prevent further insertion of the sheath into the bone hole. Such a configuration can be particularly advantageous with certain types of bone wherein it is desired to prevent the sheath from falling into the bone hole. For example, the use of a sheath having depth-stop tabs 221*a*', 221*b*' can be particularly advantageous in sub-pectoral locations since visibility can be particularly difficult.

Figure 2F:
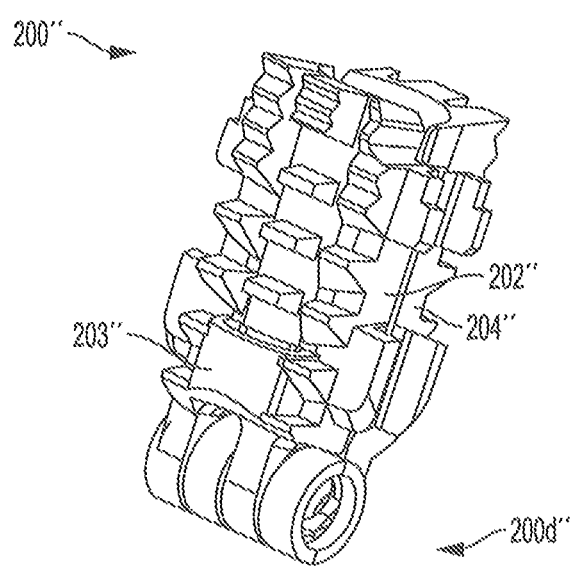
FIG. 2F is a side perspective view of yet another embodiment of a sheath for use with a biceps tenodesis system.

FIG. 2F illustrates another embodiment of a sheath 200" which is also similar to sheath 200, but that includes a suture-receiving tab 203" formed thereon. As shown, the tab 203" is in the form of a u-shaped member that extends across one of the sidewalls, e.g., sidewall 202", and that is located along a mid-portion of the sidewall 202" adjacent to a distal end 200*d*" of the sidewall 202". While only one tab 203" is shown on one of the sidewalls 202", a person skilled in the art will appreciate that the other sidewall, e.g., sidewall 204", may or may not have a suture-receiving tab 203" formed thereon. As a result of the orientation of the tab 203", the opening 205" of the tab will extend in a proximal-distal direction so as to allow a suture coupled to a tendon located distal of the sheath 200" to be advanced through the tab 203" from the distal end toward the proximal end. The trailing ends of the suture extending proximally from the tab 203" can be used to tension the tendon to pull the tendon toward the sheath 200". The trailing ends of the suture can also be wrapped around a portion of the sheath inserter tool, as discussed below, to maintain the sheath 200" on the distal end of the inserter tool. A person skilled in the art will appreciate that the suture-receiving tabs 203" can have a variety of shapes and sizes, and that various other suture-receiving features can be formed on the sheath at various locations.

Figure 3A:
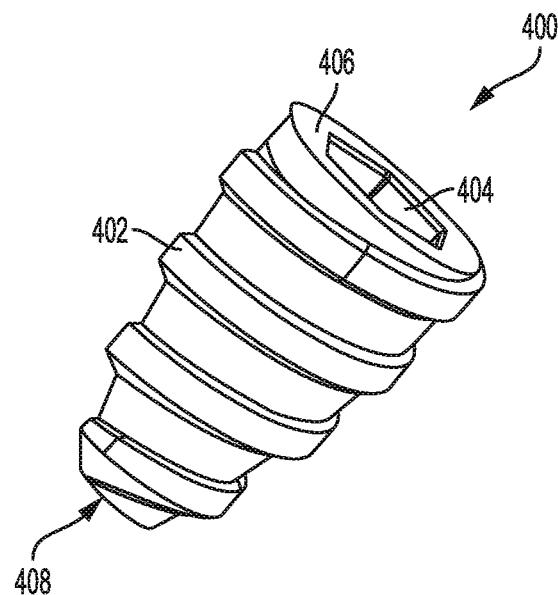
FIG. 3A is a side perspective view of the expander of FIG. 1.
Figure 3B:
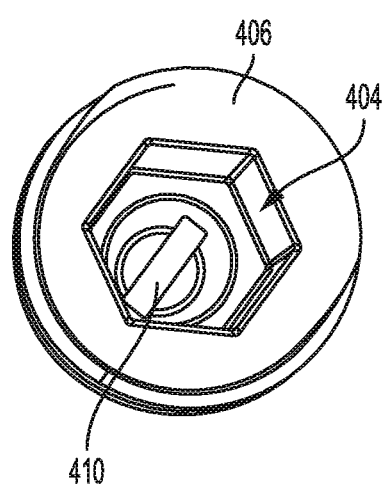
FIG. 3B is a top perspective view of the expander of FIG. 1.

As indicated above, the sheath 200 is configured to receive an expander that is effective to expand the sheath 200 to anchor the sheath 200 and tendon coupled thereto within a bone hole. As shown in FIGS. 3A and 3B, in one embodiment, the expander 400 is in the form of a threaded member or screw having a generally cylindrical shape that tapers distally inward to a reduced diameter along at least a distal portion of the length thereof. Preferably, the taper is minor along a majority of the length so that the expander 400 causes slow expansion of the sheath as it is inserted therein. The expander 400 has a thread 402 formed on the outer surface thereof and extending along the entire length of the expander 400 to facilitate engagement with the sheath 200.

The expander 400 can be fully cannulated so that it has a bore or inner lumen 404 therein. The inner lumen 404, or at least a proximal portion thereof, can have a shape and size corresponding to a shape and size of a drive feature configured to be received within the inner lumen 404 so as to rotate the expander 400. In the illustrated embodiment, the inner lumen 404 is in the form of a hexagonal drive socket configured to receive a hexagonal distal portion of the expander inserter tool, discussed below. The hexagonal distal portion of the expander inserter tool can be inserted into the inner lumen 404 as to extend along a substantial portion of the entire length of the lumen 404. A person skilled in the art will appreciate, however, that other configurations of the inner lumen 404 can be used.

As further shown in FIGS. 3A and 3B, the expander 400 can have a flat proximal facing surface 406 and a flat distal facing surface 408. The proximal surface 406 and the distal surface 408, however, can have various shapes and the shape can be configured to conform to the sheath and/or the bone surface. A length of the expander 400 can be less than, equal to, or greater than the length of the sheath 200.

The expander 400 can also include features to allow for receipt of a suture. For example, as shown in FIG. 3B, the expander 400 includes a suture receiving bar or post-410 extending thereacross for receiving a suture there around. The post can be located anywhere along the length of the expander 400 between the proximal and distal ends thereof, and it can extend at any angle. In the illustrated embodiment, the post 410 extends substantially perpendicular to a longitudinal axis of the expander 400.

A person skilled in the art will appreciate that the expander can have a variety of other configurations, and the expander can be configured to be non-rotatably inserted into the sheath, rotatably inserted into the sheath, or partially non-rotatably and partially rotatably inserted into the sheath. For example, the expander can include a proximal portion having threads formed thereon and a distal portion that is non-threaded and free of surface features. In use, the non-threaded distal portion of the expander can be non-rotatably advanced into the sheath. Once the distal portion is fully disposed within the sheath, the expander can then be rotated to thread the proximal portion into the sheath. The sheath can include corresponding threads along an entire inner surface thereof, or along on a proximal portion of the inner surface thereof, for mating with the threads on the expander.

As indicated above, the sheath 200 can be delivered into a bone hole using the sheath inserter tool 100. The sheath inserter tool 100 is shown in more detail in FIG. 4A, and as shown the tool generally includes a cannulated outer shaft 102, an inner shaft 104 that extends through the outer shaft 102, and a cannulated handle 106 that is mated to both the outer and inner shaft 102, 104. The outer shaft 102 has a proximal end 102p that fixedly mates to the handle 106 and a distal end 102d having first and second prongs 108a, 108b extending distally therefrom. In the illustrated embodiment, the proximal end 102p includes threads 110 formed thereon that threadably engage corresponding threads 106t (shown in FIG. 4D) formed within the handle 106 to fixedly mate the outer shaft 102 to the handle 106. Various other mating techniques can be used, such as a snap-fit or other mechanical interlock. The inner shaft 104 also has a proximal end 104p that fixedly mates to the handle 106, but that is freely rotatable relative to the handle 106 to allow the handle 106 to rotate and threadably engage the outer shaft 102.

The handle can have a variety of configurations, but in the illustrated embodiment it has a generally elongate cylindrical shape with an inner lumen extending therethrough. A proximal end of the handle can be generally planar for allowing a mallet to be applied thereto for advancing the anchor coupled to the tool into a bone hole. The outer surface of the handle can have any shape and size to facilitate grasping. As indicated above, an inner lumen of the handle can be configured to receive the proximal ends of the outer and inner shafts 102, 104. The configuration of the inner lumen will be discussed in detail below.

The handle can include features for mating a suture to the handle 106. In the illustrated embodiment, the handle includes opposed wings 106a, 106b that have a suture receiving channel 106s formed therearound (shown in FIG. 4D) for receiving a suture coupled to the implant. Thus, when an implant is being inserted through tissue and into a bone hole, the trailing ends of the suture coupled to the implant can be tensioned and wrapped around one of the wings 106a, 106b. In another embodiment, one or more suture receiving elements can be located on the outer shaft, rather than on the handle. Such a configuration allows the handle and the inner shaft to be removed, leaving the outer shaft with the suture and sheath coupled thereto.

Figure 4A:
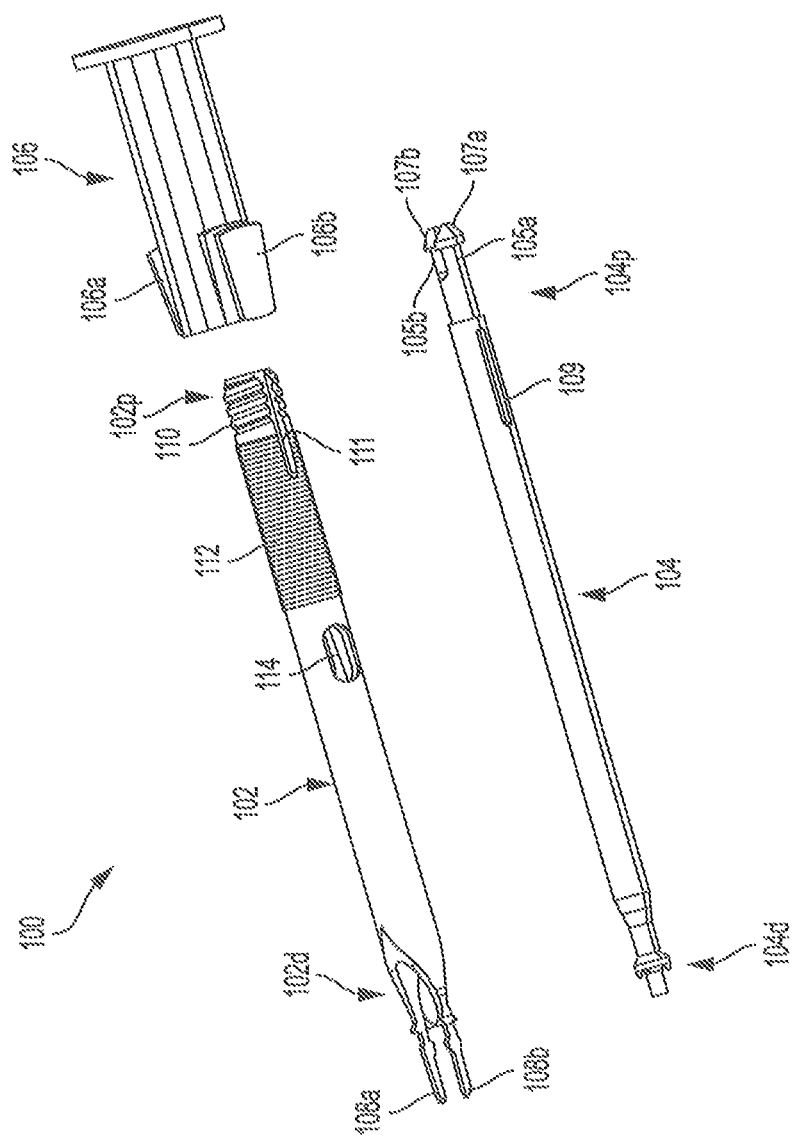
FIG. 4A is a perspective view of another embodiment of a sheath inserter tool.

Referring back to FIG. 4A, the outer shaft 102 can have a variety of configurations. The illustrated proximal end 102p of the outer shaft 102 is shown having a knurled or other textured surface 112 to facilitate grasping thereof. FIG. 4A also illustrates a window 114 formed in a sidewall of the outer shaft 102 to enable viewing of the inner shaft 104 disposed therein. The window 114 can be formed at any location along the length of the outer shaft 102, and the outer shaft 102 can include any number of windows formed therein. As indicated above, the proximal end 102p of the outer shaft 102 includes threads 110 formed on an outer surface thereof for engaging corresponding threads 106t formed within a distal portion of the inner lumen extending through the handle 106, as shown in FIG. 4D. The threaded engagement allows the handle 106, with the inner shaft 104 coupled thereto, to be advanced distally during threaded engagement with the outer shaft 102, thereby advancing a distal end of the inner shaft 104 into engagement with the sheath, as will be discussed in more detail below. Threading of the handle 106 onto the outer shaft 102 will also align the distal end of the inner shaft 104 with the sheath 200 and the outer shaft 102, as will also be discussed in more detail below.

Figure 4B:
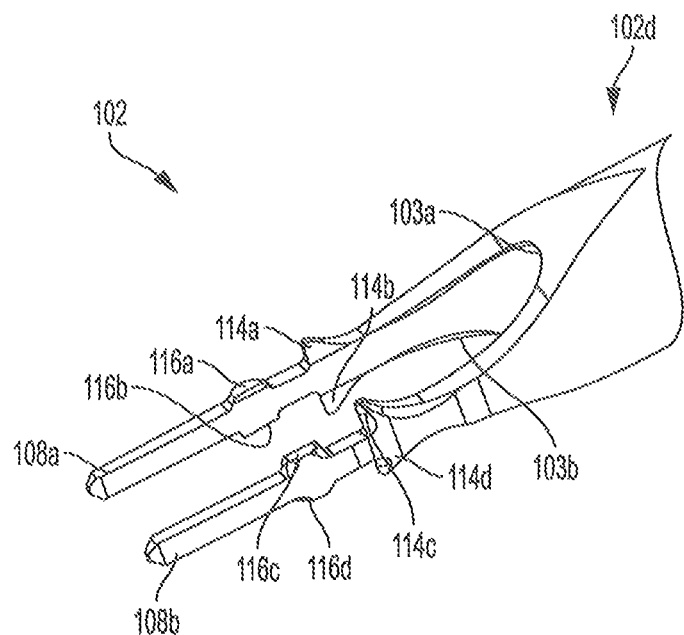
FIG. 4B is a side perspective view of a distal end of an outer shaft of the sheath inserter tool of FIG. 4A.

The distal end 102d of the outer shaft 102 is shown in more detail in FIG. 4B, and as shown the distal end 102d tapers inward in the distal direction and has opposed U-shaped cutouts 103a, 103b formed therein such that the distal end 102d includes first and second opposed arms or prongs 108a, 108b extend distally therefrom and configured to extend along the opposed slots in the sheath 200.

While the prongs 108a, 108b can have a variety of configurations and features, in the illustrated embodiment each prong 108a, 108b is in the form of elongate pin or rod that is integrally formed with the outer shaft 102 or fixedly attached to the outer shaft 102. Each prong 108a, 108b is shown having a proximal portion with a width that tapers inward and then flares outward to form a pair of proximal boss 114a, 114b, 114c, 114d. Each prong 108a, 108b also has a distal portion having a generally elongate shape with a substantially square or rectangular cross-section and a substantially constant diameter with a rounded or tapered distal tip. The proximal bosses 114a, 114b, 114c, 114d on the prongs 118a, 118b can abut against the proximal or upper tabs 216a, 216b, 216c, 216d on the sheath 200 to prevent proximal movement of the sheath when mated to the sheath inserter tool 100. A pair of distal bosses 116a, 116b, 116c, 116d is formed at a location distal of the proximal bosses 114a, 114b, 114c, 114d around a mid-portion of each prong 118a, 118b. Each of the bosses 116a, 116b, 116c, 116d is in the form of a protrusion extending outward from opposite sides of the prong 108a, 108b.

Figure 4C:
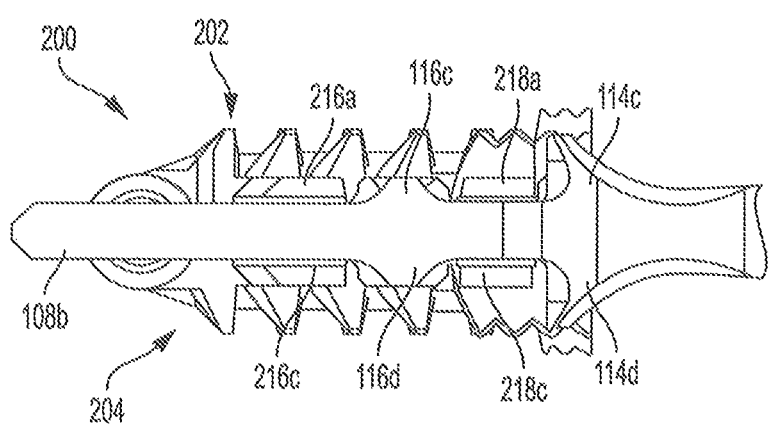
FIG. 4C is a side view of the distal end of the outer shaft of the sheath inserter tool of FIG. 4B coupled to the sheath of FIG. 1.
Figure 4D:
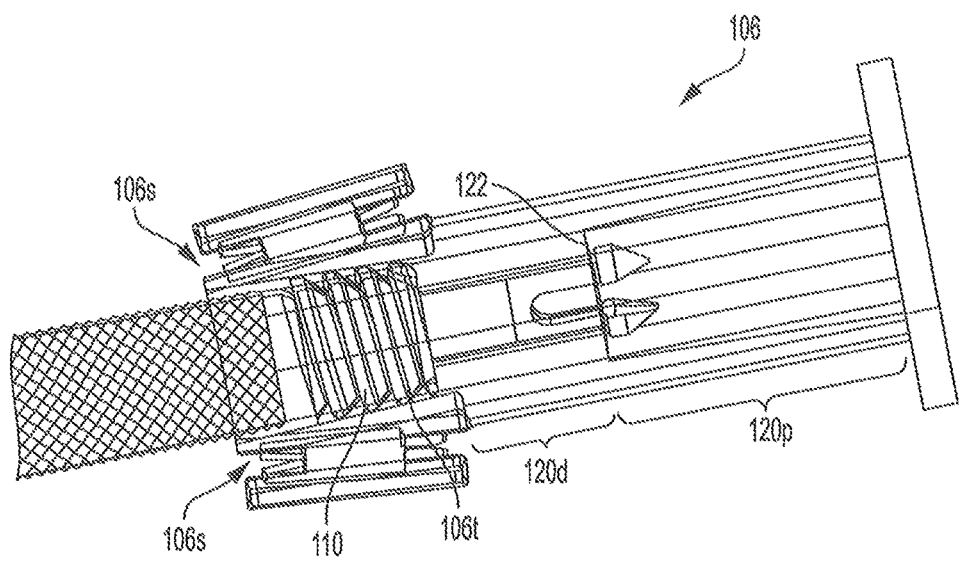
FIG. 4D is a side perspective view of a handle portion of the sheath inserter tool of FIG. 4A.

When the sheath 200 is mated to the sheath inserter tool 100, as shown in FIG. 4C, the upper and central tabs 216a, 218a on the first sidewall 202 and the upper and central tabs 216c, 218c on the second sidewall 204 will engage the second prong 108b therebetween, and while not shown the upper and central tab 216b, 218b on the first sidewall 202 and the upper and central tabs 216d, 218d on the second sidewall 204 will engage the first prong 108a therebetween. Due to the elongate generally rectangular configuration of the tabs and the prongs being engaged therebetween, the sheath 200 is prevented from rotating as a unit relative to the sheath inserter tool 100.

As further shown in FIG. 4C, the upper tab 216a on the first sidewall 202 will be seated between proximal boss 114c and distal boss 116c on the second prong 108b, and upper tab 216c on the second sidewall 204 will be seated between proximal boss 114d and distal boss 116d on the second prong 108b. While not shown, upper tab 216b on the first sidewall 202 will be seated between proximal boss 114a and distal boss 116a on the first prong 108a, and upper tab 216d on the second sidewall 204 will be seated between proximal boss 114b and distal boss 116b on first prong 108a. As a result, the sheath 200 is prevented from moving proximally relative to the prongs 108a, 108b.

As further shown in FIG. 4C, when the sheath 200 is mated to the sheath inserter tool 100, the prongs 108a, 108b will extend a distance beyond the distal end of the sheath 200. Such a configuration allows a tendon to be wrapped around the distal end of the sheath 200 and received between the prongs 108a, 108b, and it allows the prongs 108a, 108b to guide the sheath 200 into a bone hole.

Referring back to FIG. 4A, the inner shaft 104 of the sheath inserter tool 100 can also have a variety of configurations, but is generally in the form of an elongate shaft having a proximal end 104p that is mated to the handle 106, and a distal end 104d that mates to the sheath 200. The proximal end 104p can mate to the handle 106 using a variety of techniques, but in an exemplary embodiment the proximal end 104p is fixedly, but freely rotatably mated to the handle 106. In the illustrated embodiment, the proximal end 104p of the inner shaft 104 includes a slot formed therein that defines two deflectable arms or fingers 105a, 105b. Each arm or finger 105a, 105b has a flange 107a, 107b on the proximal-most end thereof. The handle 106 is configured mate to the proximal end 104p of the inner shaft 104 using a snap-fit arrangement. As shown in FIG. 4D, the inner lumen extending through the handle 106 has a portion located proximal of the threads 106t that includes a proximal section 120p with a large diameter and a mid-section 120d with a reduced diameter, such that a step 122 is formed therebetween. The diameter of mid-section 120d is configured to receive the inner shaft 104 and to cause the fingers 105a, 105b on the proximal end of the inner shaft 104 to deflect inward when passed therethrough. Once the flanges 107a, 107b extend proximally past the step 122, the fingers 105a, 105b are allowed to deflect outward back to their resting position, in which the flanges 107a, 107b will engage the step 122 to prevent removal of the inner shaft 104 from the handle 106. The step 122 will also prevent distal movement of the inner shaft 104 relative to the handle 106. The handle 106 will remain free to rotate relative to the inner shaft 104, thus allowing the handle 106 to be threaded onto the outer shaft 102 with the inner shaft 104 coupled thereto.

The inner shaft 104 can also include alignment features formed thereon for aligning the inner shaft with the outer shaft 102, thereby aligning the distal end 104d of the inner shaft 104 with the sheath 200 coupled to the outer shaft 102. As shown in FIG. 4A, the inner shaft 104 includes opposed elongate protrusions (only one protrusion 109 is shown) formed on opposed sides of a proximal end thereof. The outer shaft 102 includes corresponding cut-outs or slots (only one slot 111 is shown) formed in opposite sides thereof for slidably receiving the protrusions 109 therein.

Figure 4E:
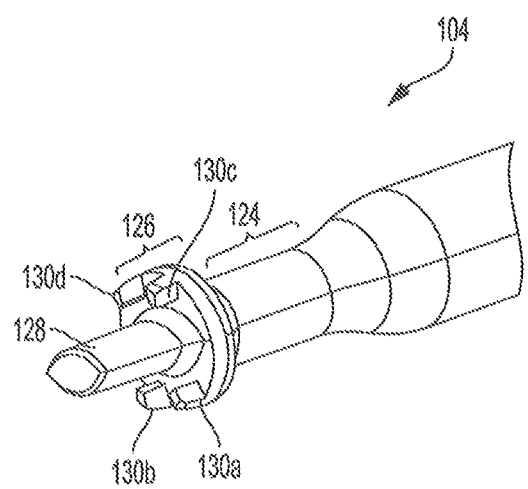
FIG. 4E is a side perspective view of a distal end of an inner shaft of the sheath inserter tool of FIG. 4A.

The distal end of the inner shaft 104 is shown in more detail in FIG. 4E, and as shown the distal end has a reduced diameter portion 124 and an increased diameter portion in the form of a radial flange 126 having a circular shape. The diameter of the flange 126 can be substantially the same as the diameter of the sheath 200, and the flange 126 can have a substantially planer distal-facing end surface that abuts up against the proximal end of the sheath 200. The end surface can include one or more protrusions formed thereon for mating with the sheath. As shown in FIG. 3E, the end surface includes a central protrusion 128 that is configured to be received between the sidewalls of the sheath 200. The central protrusion 128 can thus have a size and shape that generally matches the size and shape of the inner lumen of the sheath 200. In the illustrated embodiment, the central protrusion 128 has a generally oblong cross-sectional shape. The non-circular geometry can be advantageous as it will prevent rotation of the inner shaft 104 relative to the sheath 200.

Figure 4F:
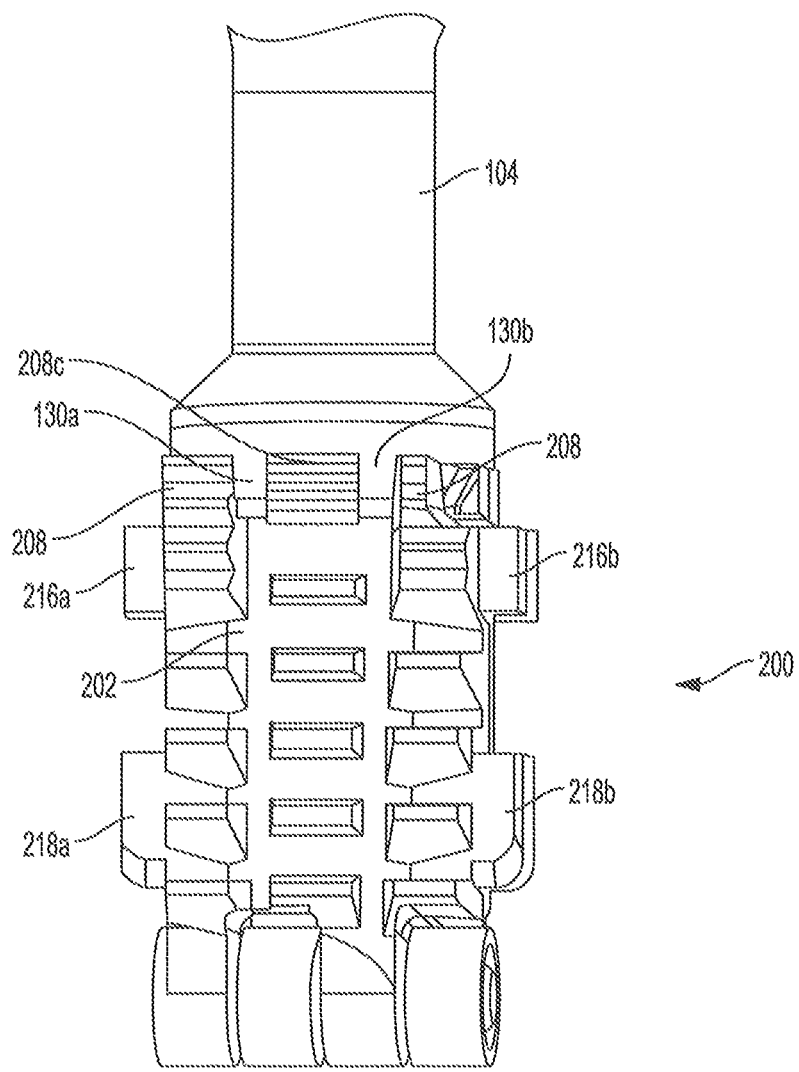
FIG. 4F is a side perspective view of the distal end of the inner shaft of FIG. 4E coupled to the sheath of FIG. 1.

The end surface of the inner shaft 104 can also include one or more protrusions formed adjacent an outer perimeter thereof and configured to extend along an outer surface of each sidewall of the sheath. As shown in FIG. 3E, the end surface includes four protrusions 130a-d formed thereon, with two protrusions 130a, 130b being positioned on a first side to extend along an outer surface of the first sidewall 202 of the sheath 200, and the other two protrusions 130c, 130d being positioned on a second, opposite side to extend along an outer surface of the second sidewall 204 of the sheath 200. The four protrusions 130a-d have a length and diameter that is significantly less than a length of the central protrusion 128, as the central protrusion is intended to occupy a substantial portion of the inner lumen of the sheath 200. The four protrusions 130a-d can also vary in shape, but in an exemplary embodiment each protrusion has a generally rectangular or square cross-sectional shape and is configured to extend between teeth in the proximal-most row of teeth on the sidewalls of the sheath 200. In particular, as shown in FIG. 4F, two of the protrusions 130a, 130b located on one side of the inner shaft 104 will extend between the proximal-most central tooth 208c and an outer tooth 208. Such positioning of the protrusions 130a, 130b between the teeth can further assist in preventing rotation of the inner shaft 104 relative to the sheath 200.

Referring back to FIG. 1, when the system 10 is assembled, the sheath 200 is positioned at the distal end 102d of the outer shaft 102 such that the first and second prongs 108a, 108b extend along the elongate slots 200a, 200b in the sheath 200 and extend beyond the distal end 200d of the sheath 200. The central protrusion 128 on the inner shaft 104 will extend into the central lumen of the sheath 200, and the outer protrusions 130a-d on the inner shaft 104 will extend around the outer sidewalls of the sheath 200. The upper and lower tabs 216a-d, 218a-d on the sheath 200 will engage the prongs 108a, 108b so as to prevent rotation of the sheath 200 about an axis extending laterally across a mid-portion of the sheath 200. The upper tabs 216a-d on the sheath 200 will be engaged between the proximal and distal bosses 116a-d on the prongs 108a, 108b.

With continued reference to FIG. 1, as indicated above the system can also include an expander inserter tool 300 for inserting the expander 400 through the sheath inserter tool 100 and into the sheath 200. In an exemplary embodiment, as shown in FIG. 1, the expander inserter tool 300 is in the form of a screw driver having a drive tip configured to extend into the expander 400. In particular, the expander inserter tool 300 has a handle 302 and an elongate shaft 304 extending distally from the handle 302. The distal end of the elongate shaft 304 includes a drive tip 306 formed thereon for engaging the lumen 404 in the expander 400. In the illustrated embodiment, the drive tip 306 has a hexagonal configuration for extending into a corresponding hexagonal drive socket (shown in FIG. 3B) formed in the expander 400 to thereby allow the expander inserter tool 300 to rotate the expander 400. However, one skilled in the art will appreciate that the drive tip 306 can have any other configuration so as to fit within the inner lumen of the expander 400 and rotatably engage the expander 400.

Figure 5A:
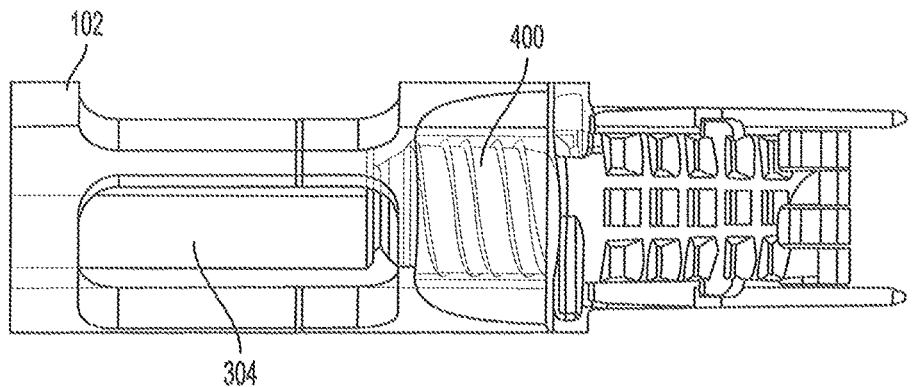
FIG. 5A is a side, partially transparent view of the sheath inserter tool of FIG. 4A having the sheath of FIG. 1 mounted thereon and having the expander of FIG. 1 mounted therein.
Figure 5B:
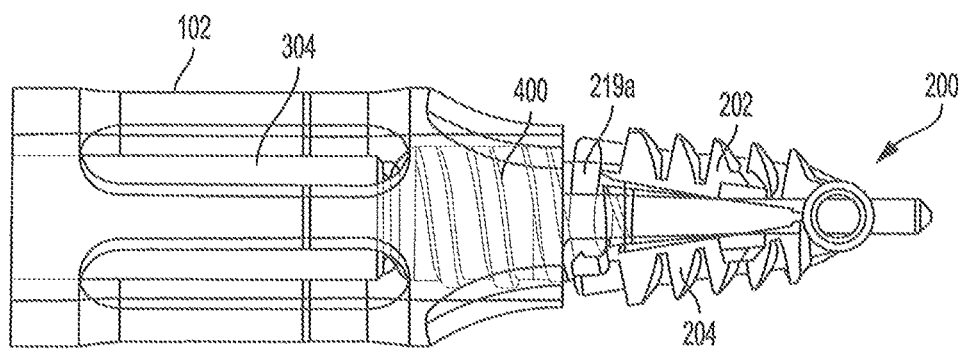
FIG. 5B is a side, partially transparent view of the assembly shown in FIG. 5A, with the expander being advanced into the sheath.
Figure 6:
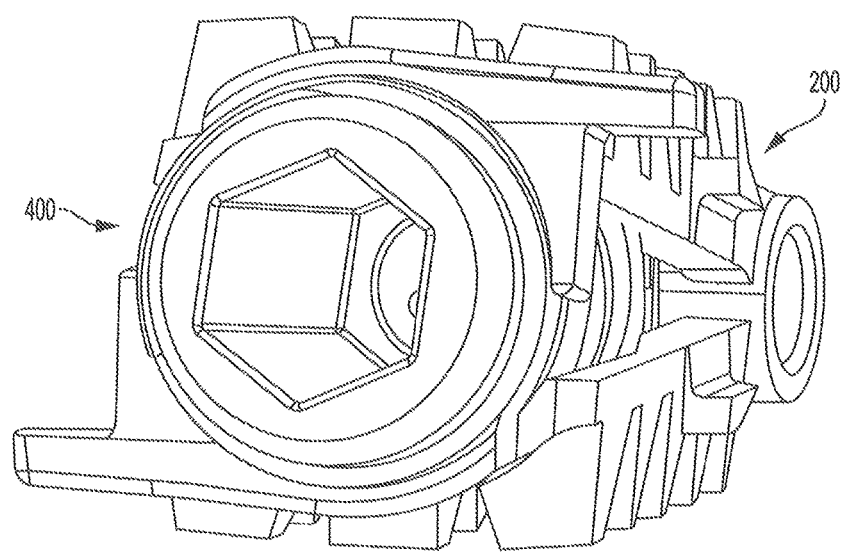
FIG. 6 is a top perspective view of the sheath of FIG. 1 having the expander of FIG. 1 fully disposed therein.
Figure 7:
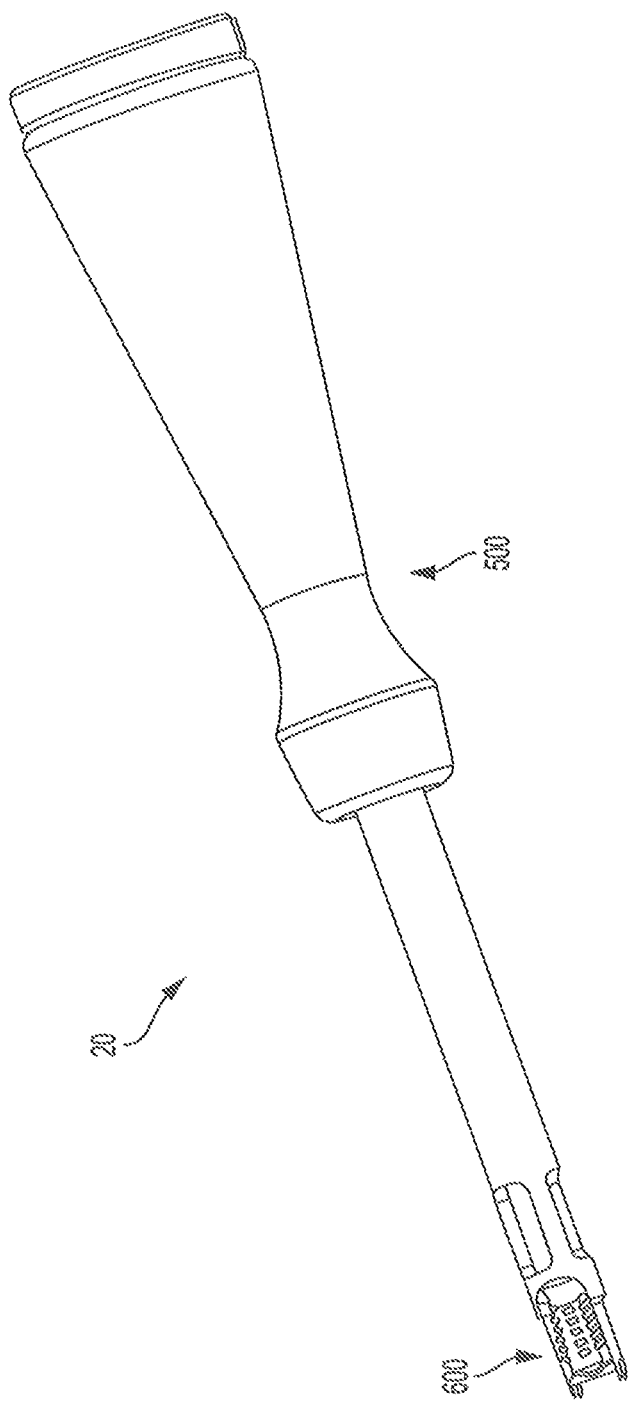
FIG. 7 is a side perspective view of another embodiment of a sheath inserter tool and sheath for use with a biceps tenodesis system.

When assembled, the expander inserter tool 300 extends through the outer shaft 102 of the sheath inserter tool 100 (with the inner shaft 104 being removed). The expander inserter tool 300 can rotate freely relative to the outer shaft 102 so as to thread the expander 400 into the sheath 200. FIGS. 5A and 5B illustrate the expander inserter tool 300 positioned within the outer shaft 102 of the sheath inserter tool 100 and about to advance the expander 400 into the sheath 200. As the expander 400 is introduced into the sheath 200, the retention boss (only one boss 219a is shown) will engage the threads on the expander 400. Such a configuration can reduce the likelihood for intra- or post-operative disengagement between the sheath and the expander. Since the diameter of the expander 400 is greater than an inner diameter of the sheath 200 in the collapsed position, the expander 400 will cause the sidewalls 202, 204 of the sheath 200 to pivot about the pivot pin and thereby expand outward to into bone. The assembly will thus engage the bone thereby anchoring the tendon within the bone hole. FIG. 6 illustrates a proximal end view of the sheath and expander in the fully implanted configuration.

FIGS. 7-10 illustrate another embodiment of a biceps tenodesis system 20 that includes a sheath inserter tool 500 having an expandable sheath 600 coupled thereto. The system 20 can be used with the expander inserter tool and expander described above, and thus these components are not discussed with respect to this embodiment. In this embodiment, the sheath 600 has two separate and distinct halves that are not mated, but rather that have cross-bars that are held together by the sheath inserter tool 500 and that receive a tendon therearound. The sheath inserter tool 500 can include various feature for mating with and interacting with the sheath.

Figure 8A:
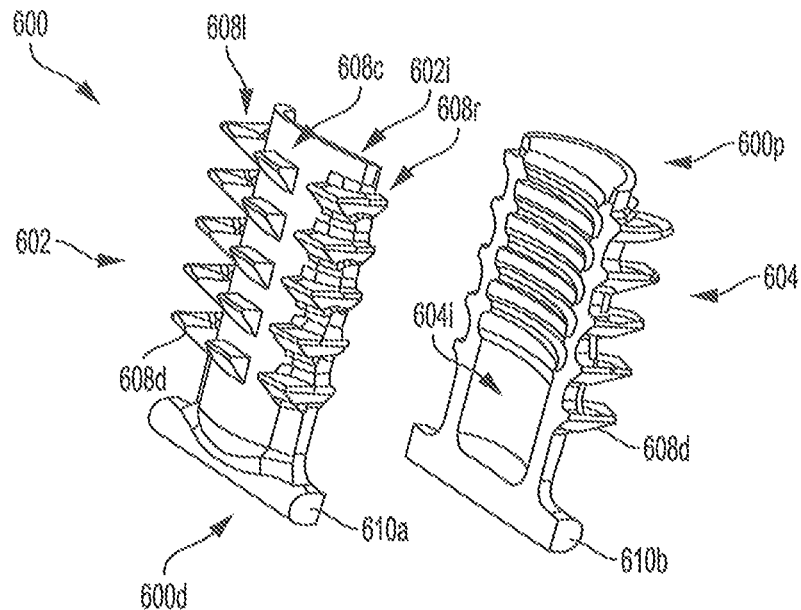
FIG. 8A is an exploded side perspective view of the sheath of FIG. 7.
Figure 8B:
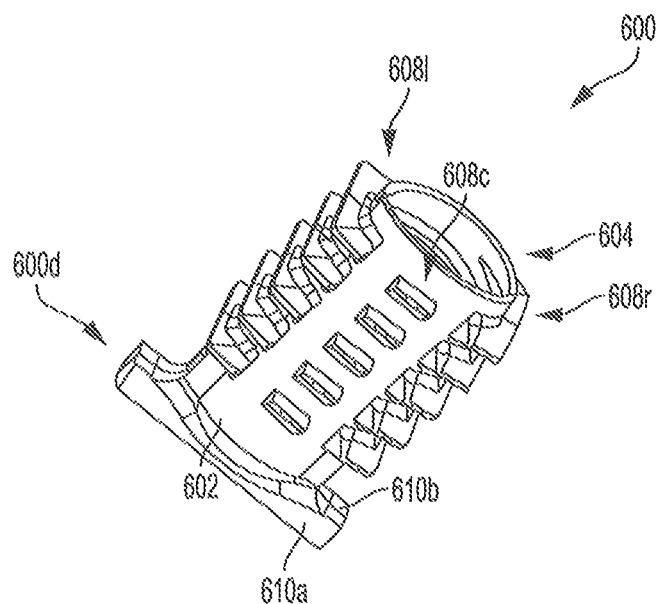
FIG. 8B is a side perspective view of the sheath of FIG. 7.

The sheath 600 is shown in more detail in FIGS. 8A-8B and as shown, the sheath 600 has first and second sidewalls 602, 604 that are configured to couple, but not mechanically mate, to one another. Each sidewall 602, 604 has a substantially hemi-cylindrical shape with an inner concave surface 602i, 604i configured to seat the expander, and an outer convex surface with bone-engaging surface features formed thereon for engaging bone within a bone hole. The bone-engaging surface features can have the same configuration as discussed above with respect to sheath 200, or they can have other configurations. As best shown in FIG. 8B, in this embodiment each sidewall 602, 604 has three columns of teeth spaced longitudinally along the sidewall between the proximal and distal ends, namely a central column of teeth 608c, and left and right side columns of teeth 608l, 608r. Each tooth is generally rectangular in shape, however a distal facing sidewall 608d of each tooth can be angled toward the proximal end 600p to facilitate insertion into the bone hole, and to prevent proximal movement of the sheath 600 once implanted in the bone hole.

As indicated above, a distal end 600d of each sidewall 602, 604 can include a cross-bar 610a, 610b formed thereon. Each cross-bar 610a, 610b can extend substantially perpendicular to the longitudinal axis of the sheath 600 and can have a length that is substantially the same as or more preferably greater than a width of the sidewalls of the sheath 600. Such a configuration can allow the cross-bars 610a, 610b to be seated within a notch formed in prongs on the sheath inserter tool 500, discussed below. The illustrated cross-bars 610a, 610b have a substantially cylindrical shape with a planar inner surface such that the cross-bars will form a complete cylinder when the sidewalls 602, 604 are seated adjacent to one another. A tendon or ligament can be positioned around the cross-bars 610a, 610b and can extend along the outer surface of each sidewall 602, 604. In use, when an expander 400 (shown in FIG. 1) is inserted into the sheath 600, the sheath inserter tool 500 will maintain the cross-bars 610a, 610b in a coupled configuration and thus the sidewalls 602, 604 will pivot about a longitudinal axis of the cross-bars 610a, 610b to move apart and engage bone, as will be discussed in further detail below.

As indicated above, the sheath inserter tool 500 in this embodiment can include various features for mating with and interacting with the sheath 600. As shown in more detail in FIGS. 9A and 9B, the sheath inserter tool 500 generally includes an outer shaft 510, an inner shaft 520 configured to extend through the outer shaft 510, and a handle 530 for coupling to the outer and inner shafts 510, 520. The sheath inserter tool 500 can include any of the features described above with respect to the sheath inserter tool 100. In general, the outer shaft 510 is similar to the above embodiment and includes opposed first and second prongs 502, 504 extending distally from a distal end 510d thereof. A proximal end 510p of the outer shaft 510 is configured to fixedly mate to the handle 530, e.g., by a press-fit or other known techniques, such that the outer shaft 510 and the handle 530 function as a unit. In this embodiment, the handle 530 has a generally elongate shape with an outer diameter that increases at a distal end 530d and that tapers radially outward toward the proximal end 530p, however the handle 530 can have a variety of shapes and sizes.

The prongs 502, 504 extending from the distal end 510d of the outer shaft 510 can each have a configuration similar to the prongs described above, however in this embodiment each prong 502, 504 includes a notch 502n, 504n formed in the distal-most end thereof for seating the cross-bars 610a, 610b. As shown, each notch 502n, 504n can have a generally circular shape that corresponds to a shape of the cross-bars 610a, 610b when mated. The length of the prongs 502, 504 are configured such that the prongs 502, 504 will maintain the sheath 600 in a position in which a proximal-most end 600p of the sheath 600 is aligned with a shoulder 512 formed on the distal end 510d of the outer shaft 510. The shoulder 512 is configured to abut against an outer surface of bone when the prongs 502, 504 are positioned within a bone hole to limit insertion of the outer shaft 510 into the bone hole. The prongs 502, 504 will thus position the sheath 600 at a desired depth within the bone hole.

The prongs 502, 504 can include other features similar to those described above. For example, as shown in more detail in FIG. 9B, each prong 502, 504 can include first and second bosses (only two bosses 506a, 506b on prong 502 are shown) formed on an internal surface thereof. As shown, the first boss 506a is positioned at or near the proximal end of the prong 502 and it can be in the form of a protrusion that is configured to extend between the left row of teeth 608L on each sidewall 602, 604 of the sheath 600. The second boss 506b is located distal of the first boss 506a, e.g., around a mid-portion of the prong 502, and it can extend between the right row of teeth 608R on each sidewall 602, 604 of the sheath 600. The bosses 506a, 506b can function to prevent distal movement of the sheath 600 with respect to the sheath inserter tool 500, i.e., to prevent the sheath 600 from falling into the bone hole. While FIG. 9B only illustrates the bosses 506a, 506b on the first prong 502, a person skilled in the art will appreciate that the second prong 504 can include a corresponding set of bosses.

Figure 9A:
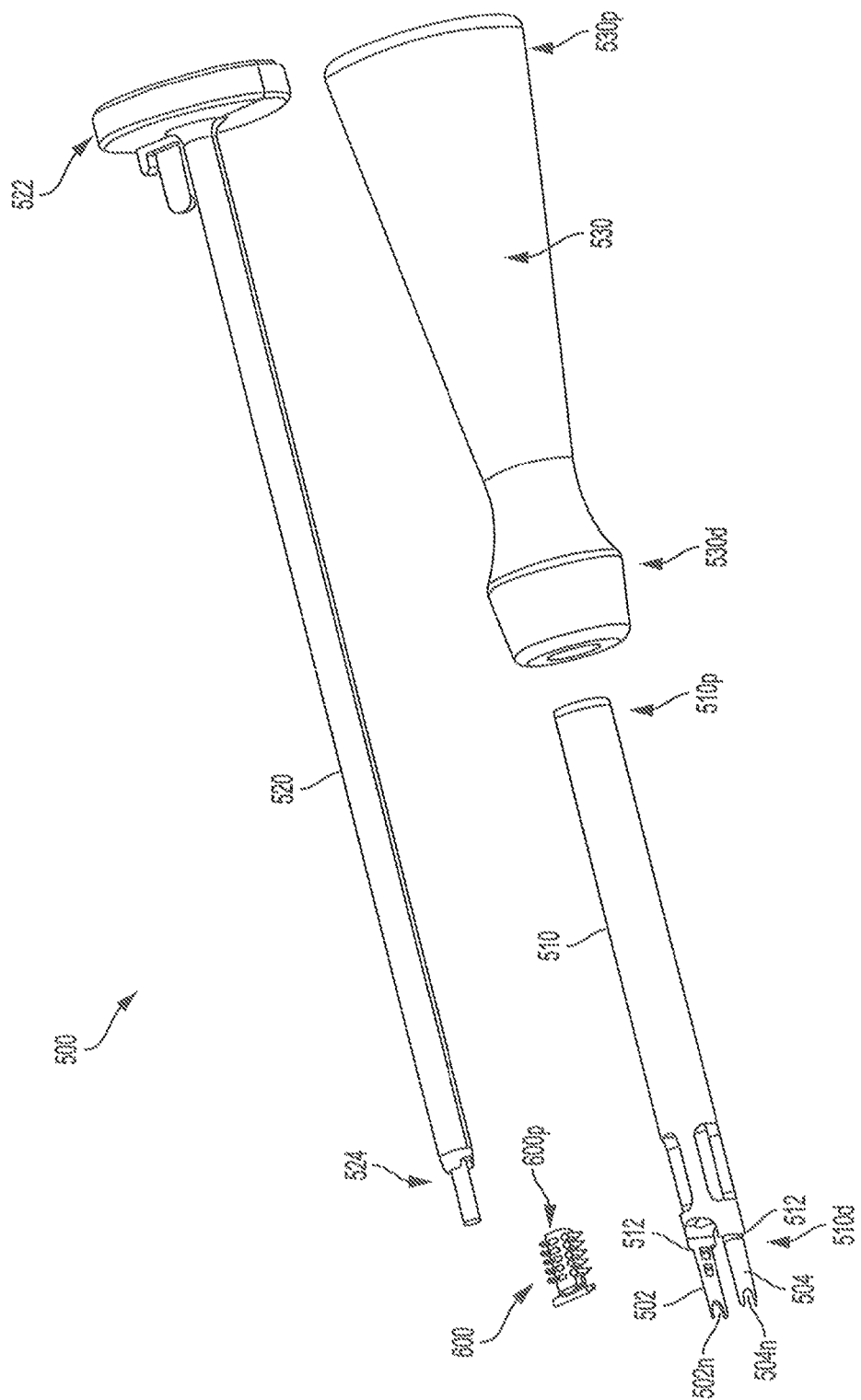
FIG. 9A is an exploded side perspective view of the sheath inserter tool and sheath of FIG. 7.
Figure 9B:
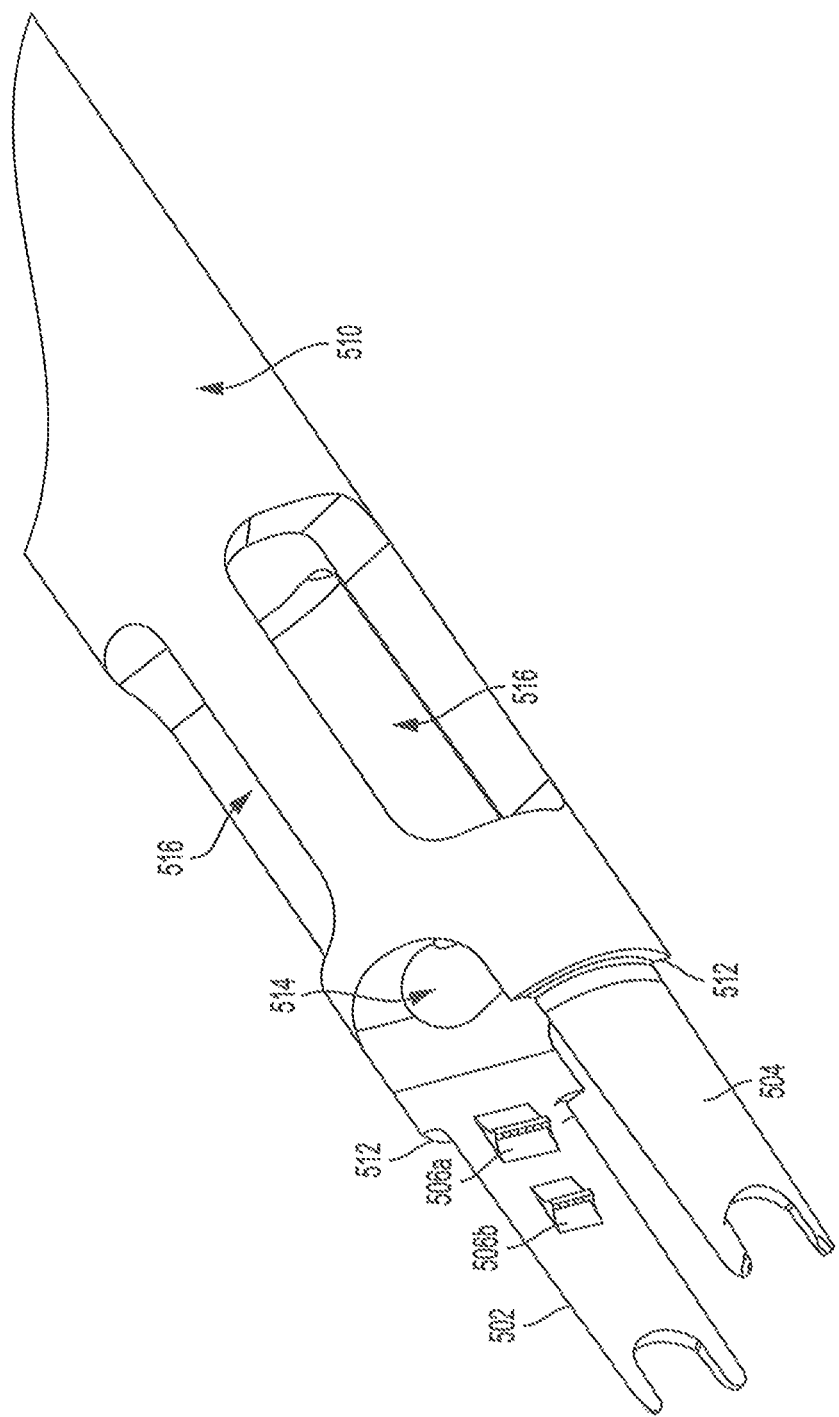
FIG. 9B is a side perspective view of a distal end of the sheath inserter tool of FIG. 7.

FIG. 9B also illustrates shaped opening 514 at the distal end of the inner lumen in the outer shaft 510 and located at the proximal end of the prongs 502, 504. The shaped opening 514 has a shape that conforms to an outer surface of the inner shaft 520 at the distal end so as to receive the inner shaft 520 therethrough and to maintain the inner shaft 520 in longitudinal alignment with the sheath 600 during advancement of the inner shaft 520 into the sheath 600. In the illustrated embodiment, the shaped opening 514 is circular, however the opening can have various configurations.

FIG. 9B also illustrates several windows or cut-outs 516 formed in the outer shaft 510 adjacent the distal end for enabling viewing into the inner lumen, and in particular for enabling viewing of the inner shaft 520 as well as the expander inserter tool when positioned within the outer shaft 510. A person skilled in the art will appreciate that the outer shaft 510 can have any number of windows or cut-outs formed therein at various locations, as discussed above with respect to outer shaft 102.

As indicated above, the sheath inserter tool 500 also includes an inner shaft 520 that is configured to extend through the outer shaft 510. Referring back to FIG. 9A, the inner shaft 520 generally has an elongate cylindrical shape with a proximal end having a handle 522 formed thereon and a distal end having a plug or distal tip 524 configured to extend into the sheath 600. The handle 522 can have various configurations, but as shown the handle 522 is generally disc-shaped with a planar proximal end surface for receiving a force from a hammer if necessary. When the inner shaft 520 is inserted into the outer shaft 510, the handle 522 on the inner shaft 520 will abut the proximal end surface of the handle 530 coupled to the outer shaft 510, thereby limiting an insertion depth of the distal tip 524 on the inner shaft 520 into the sheath 600.

Figure 9C:
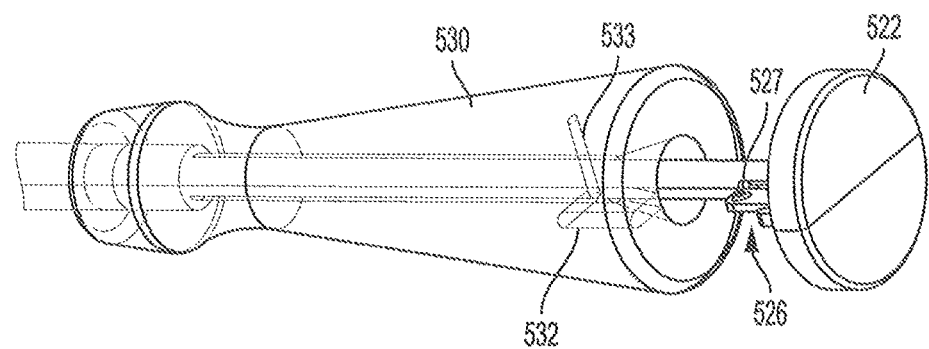
FIG. 9C is a side perspective view of a handle portion of the sheath inserter tool of FIG. 7.

As shown in FIG. 9C, the handle 522 on the inner shaft 520 can include an anti-rotation lock 526 formed thereon and extending distally from a distal-facing surface thereof. The anti-rotation lock 526 can be configured to extend into a corresponding slot or bore 532 formed in the proximal end of the handle 530 coupled to the outer shaft 510 to thereby prevent rotation of the inner shaft 520 relative to the outer shaft 510. The anti-rotation lock 526 and bore 532 also facilitate alignment of the distal tip 524 with the sheath 600. As further shown in FIG. 9C, the anti-rotation lock 526 can include a protrusion or boss 527 formed therein that is configured to engage a corresponding detent or bore 533 extending from the bore 532. The boss 527 and bore 533 create a frictional detect between the handle 522 on the inner shaft 520 and the handle 520 on the outer shaft 510.

Figure 9D:
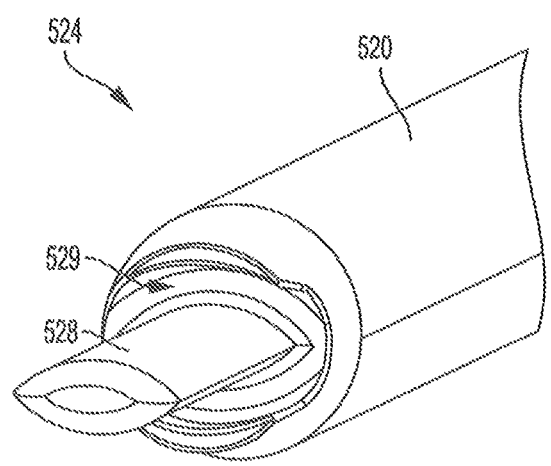
FIG. 9D is an end perspective view of a distal end of an inner shaft of the sheath inserter tool of FIG. 7.

The distal tip 524 of the inner shaft 520 is shown in more detail in FIG. 9D, and as shown the distal tip 524 has a protrusion 528, similar to the protrusion 128 discussed above with the previous embodiment. The illustrated protrusion 528 has a generally oval-shaped cross-section such that it corresponds to a shape of the inner lumen of the sheath 600 when the sidewalls 602, 604 are coupled and the sheath 600 is in the closed configuration.

As further shown in FIG. 9D, the inner shaft 520 can also include a groove 529 formed in the distal end thereof and extending circumferentially around the distal tip 528. The groove 529 can have a shape and size that corresponds to a shape and size of the proximal end of each sidewall 602, 604 of the sheath 600 such that the groove 529 is configured to seat the proximal end of each sidewall 602, 604 of the sheath 600. As a result of the groove 529, the outer sidewalls of the inner shaft 520 will extend around the proximal ends of the sidewalls 602, 604 of the sheath 600, thereby preventing movement (e.g., opening) of the sheath 600 when the inner shaft 520 is coupled to the sheath 600. The inner shaft 520 will thus maintain the sheath 600 in the closed position.

FIG. 10 illustrates the sheath 600 and sheath inserter tool 500 fully assembly, with the distal tip (not shown) of the inner shaft 520 fully inserted into the sheath 600. As shown, the cross-bars 610a, 610b on the sheath 600 are seated within the notches 502n, 504n in the distal ends of the prongs 502, 504, and the bosses (only two bosses 506a, 506 are shown) on the prongs 502, 504 extend between the teeth (bosses 506a, 506b are shown extending between the right teeth 608L) on the sheath 600 to prevent the sheath 600 from moving distally relative to the prongs 502, 504. The proximal end of the sheath 600 is aligned with the shoulder 512 on the outer shaft 510, and the proximal end of each sidewall 602, 604 extends into the groove 529 in the inner shaft 520. The inner shaft 520 will thus maintain the sidewalls 602, 604 in the closed position during insertion into a bone hole. The groove 529 seating the proximal end of each sidewall 602, 604 can also function to apply a distally-directed force on the sheath 600 during insertion into a bone hole so as to alleviate some of the force applied to the cross-bars 610a, 610b. Once the sheath 600 is fully inserted into the bone hole, the inner shaft 520 can be removed from the outer shaft 510 and the expander inserter tool 300 can be advanced through the outer shaft 510 to drive the expander 400 into the sheath 600 and thereby expand and anchor the sheath 600, and a tendon positioned there around, within the bone hole. As the sheath 600 is expanded, the bosses will become disengaged with the teeth on the sheath sidewalls 602, 604, thus allowing the outer shaft 510 to be subsequently removed.

The systems described herein can be used to implant a sheath or anchor in a bone in various different ways. One exemplary method for implanting an anchor in bone, for example, to perform a biceps tenodesis surgery, is described in U.S. application Ser. No. 14/610,602, filed on Jan. 30, 2015 and entitled "Biceps Tenodesis Implants and Delivery Tools," which is hereby incorporated by reference in its entirety.

In a biceps tenodesis procedure, a biceps tendon is retrieved in a suitable manner and a size of the tendon is determined to allow a surgeon to select an appropriately sized implant and tools. Further, in some embodiments, the sheath inserter tool 100 or 500 can be used to size the tendon by using the prongs 108a, 108b or 502, 504. Tools having different sizes can have differently sized prongs or forks. After properly sizing the tendon, the proper size reamer can be used to ream a bore in the bone, e.g., the humerus. However, a person skilled in the art will appreciate that the bone hole can be formed using any suitable bone hole preparation techniques and devices.

The bone hole diameter can be sized to allow the prongs having a tendon positioned between the prongs thereof and around the sheath to be easily inserted therein. If sheath 200' is used, the depth-stop tabs 221a', 221b' on the sheath 200' can prevent over insertion of the sheath into the bone hole. In other embodiments, the outer shaft, e.g., outer shaft 102 of sheath inserter tool 100, can include laser markings formed therein for indicating the insertion. In yet another embodiment, the outer shaft, e.g., outer shaft 510 of sheath inserter tool 500, can include a shoulder 512 formed thereon having a greater diameter compared to the bone hole, so that the outer shaft 510 will be prevented from entering into the bone hole.

After a bone hole in bone is prepared, the sheath coupled to a distal end of the sheath inserter tool can be positioned adjacent to the tendon to be advanced into the bone hole. The inserter tool with the sheath coupled thereto can be advanced into the bone hole, and the inner shaft, e.g., inner shaft 104 or 520, can be removed leaving the outer shaft, e.g., outer shaft 102 or shaft 510 in place holding the sheath within the bone hole. The expander inserter tool, e.g., tool 300, can be advanced with the expander 400 coupled thereto through the outer shaft and it can be driven into the sheath. A surgeon can hold the handle coupled to the outer shaft of the sheath inserter tool so that the handle remains stationary while the expander inserter tool is rotated. The outer shaft of the sheath inserter tool will thus prevent rotation of the sheath during rotation of the expander into the sheath. The expander will cause the sheath to expand, with the proximal end expander radially outward by a distance that is greater than the distal end. The sheath will engage the bone hole with the tendon therebetween, thus anchoring the tendon within the bone hole. It should be appreciated that in some embodiments a guidewire and/or a suture can be additionally used.

A person skilled in the art will appreciate that the biceps tenodesis methods and devices disclosed herein can be used in a variety of surgical procedures to prevent trauma or damage to a tendon being attached to a bone via a bone hole. The present invention also has application in conventional joint repair surgeries.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A bone anchoring system, comprising:
   a sheath having a first sidewall with proximal and distal ends and a second sidewall with proximal and distal ends, the distal ends of the first and second sidewalls being coupled to one another by a hinge pin such that the first and second sidewalls pivot relative to one another about the hinge pin, wherein the proximal ends of the first and second sidewalls are configured to be spaced away from one another when the sheath is in an implanted configuration; and
   an elongate shaft having a distal end with a distally-extending central protrusion that extends into the sheath between the first and second sidewalls, and the distal end having at least first and second distally-extending side protrusions positioned on opposite sides of the central protrusion and extending along opposite outer sides of the first and second sidewalls such that the first and second distally-extending side protrusions prevent rotation of the first and second sidewalls about the hinge pin.

2. The bone anchoring system of claim 1, wherein the distally-extending central protrusion extends a distance beyond the first and second distally-extending side protrusions.

3. The bone anchoring system of claim 1, wherein the distally-extending central protrusion and the first and second distally-extending side protrusions define a radially extending slot therebetween that seats a proximal-most end of the first and second sidewalls.

4. The bone anchoring system of claim 1, wherein the distally-extending central protrusion has an oblong cross-sectional shape such that the distally-extending central protrusion is prevented from rotating within the first and second sidewalls.

5. The bone anchoring system of claim 1, further comprising a handle slidably coupled to a proximal end of the elongate shaft.

6. The bone anchoring system of claim 1, wherein the elongate shaft comprises proximal and distal components that are rotatably coupled to one another, the proximal component being mated to a handle.

7. A bone anchoring system, comprising:
a sheath having a first sidewall with proximal and distal ends and a second sidewall with proximal and distal ends, the distal ends of the first and second sidewalls being coupled to one another by a hinge pin such that the first and second sidewalls pivot relative to one another about the hinge pin; and
an elongate shaft having a distal end with a distally-extending central protrusion that extends into the sheath between the first and second sidewalls, and the distal end having at least first and second distally-extending side protrusions positioned on opposite sides of the central protrusion and extending along opposite outer sides of the first and second sidewalls and third and fourth distally-extending side protrusions positioned on opposite sides of the central protrusion and extending along opposite outer sides of the first and second sidewalls such that the distally-extending side protrusions prevent rotation of the first and second sidewalls about the hinge pin.

8. The bone anchoring system of claim 7, wherein the first and second outer sidewalls each have a plurality of teeth formed thereon, and wherein the first and third distally-extending side protrusions are positioned on opposite sides of a tooth formed on an outer surface of the first sidewall, and the second and fourth distally-extending side protrusions are positioned on opposite sides of a tooth formed on an outer surface of the second sidewall.

9. The bone anchoring system of claim 7, wherein the distally-extending central protrusion extends a distance beyond the first and second distally-extending side protrusions.

10. The bone anchoring system of claim 7, wherein the distally-extending central protrusion and the first and second distally-extending side protrusions define a radially extending slot therebetween that seats a proximal-most end of the first and second sidewalls.

11. The bone anchoring system of claim 7, wherein the distally-extending central protrusion has an oblong cross-sectional shape such that the distally-extending central protrusion is prevented from rotating within the first and second sidewalls.

12. The bone anchoring system of claim 7, further comprising a handle slidably coupled to a proximal end of the elongate shaft.

13. The bone anchoring system of claim 7, wherein the elongate shaft comprises proximal and distal components that are rotatably coupled to one another, the proximal component being mated to a handle.

* * * * *